United States Patent  (10) Patent No.: US 6,552,204 B1
Harrington et al. (45) Date of Patent: Apr. 22, 2003

(54) SYNTHESIS OF 3,6-DIALKYL-5,6-DIHYDRO-4-HYDROXY-PYRAN-2-ONE

(75) Inventors: Peter J. Harrington, Louisville; Lewis M. Hodges, Longmont, both of CO (US); Kurt Puentener, Basel; Michelangelo Scalone, Birsfelden, both of (CH)

(73) Assignee: Roche Colorado Corporation, Boulder, CO (US)

( * ) Notice: Subject to any disclaimer, the term of this patent is extended or adjusted under 35 U.S.C. 154(b) by 0 days.

(21) Appl. No.: 09/668,799

(22) Filed: Sep. 22, 2000

Related U.S. Application Data

(60) Provisional application No. 60/180,578, filed on Feb. 4, 2000.

(51) Int. Cl.[7] .............................. C07F 7/04; C07F 7/08; C07D 309/30
(52) U.S. Cl. ........................ 549/292; 556/435; 556/436
(58) Field of Search .................. 562/433; 549/292; 556/435, 436

(56) References Cited

PUBLICATIONS

Yoshiktsu Suzuki et al., *Bioorganic Chemistry*, 1982, 11,300–312.

*Primary Examiner*—Celia Chang
*Assistant Examiner*—Raymond Covington
(74) *Attorney, Agent, or Firm*—Townsend and Townsend and Crew LLP

(57) ABSTRACT

The present invention relates to a novel process for producing a δ-lactone of the formula:

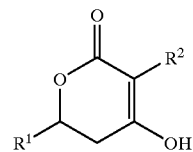

using an acyl halide of the formula:

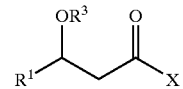

wherein $R^1$, $R^2$ $R^3$ and X are described herein. In particular, the present invention relates to a process for enantioselectively producing the δ-lactone and novel intermediates disclosed herein.

44 Claims, No Drawings

SYNTHESIS OF 3,6-DIALKYL-5,6-DIHYDRO-4-HYDROXY-PYRAN-2-ONE

CROSS-REFERENCES TO RELATED APPLICATIONS

This application claims the benefit of U.S. Provisional Application No. 60/180,578, filed Feb. 4, 2000, which is incorporated herein by reference in its entirety.

FIELD OF THE INVENTION

The present invention is directed to a process for producing 3,6-dialkyl-5,6-dihydro-4-hydroxy-pyran-2-one. In particular, the present invention is directed to an enantioselective process for producing the same.

BACKGROUND OF THE INVENTION

δ-Lactones such as 3,6-dialkyl-5,6-dihydro-4-hydroxy-pyran-2-ones are useful intermediates in the preparation of a variety of fine chemicals and pharmaceutically active compounds. For example, 5,6-dihydro-3-hexyl-4-hydroxy-6-undecyl-pyran-2-one is a well known precursor for the preparation of oxetanones such as tetrahydrolipstatin. See for example, U.S. Pat. Nos. 5,245,056 and 5,399,720, both issued to Karpf et al.; and U.S. Pat. Nos. 5,274,143 and 5,420,305, both issued to Ramig et al.

Other methods of preparing tetrahydrolipstatin use a β-hydroxy ester, e.g., methyl 3-hydroxy tetradecanoate, as an intermediate. See for example, Pommier et al., *Synthesis*, 1994, 1294-1300, Case-Green et al., *Synlett.*, 1991, 781–782, Schmid et al., Proceedings of the Chiral Europe '94 Symposium, Sep. 19–20, 1994, Nice, France, and the above mentioned U.S. Patents. Some methods of preparing oxetanones, such as those disclosed in the above mentioned U.S. Patents issued to Karpf et al., use a β-hydroxy ester as an intermediate to prepare the δ-lactone which is then used in the synthesis of oxetanones.

The stereochemistry of a molecule is important in many of the properties of the molecule. For example, it is well known that physiological properties of drugs having one or more chiral centers, i.e., stereochemical centers, may depend on the stereochemistry of a drug's chiral center(s). Thus, it is advantageous to be able to control the stereochemistry of a chemical reaction.

Many oxetanones, e.g., tetrahydrolipstatin, contain one or more chiral centers. Intermediates δ-lactone and β-hydroxy ester used in the synthesis of tetrahydrolipstatin contain one chiral center. Some syntheses of these intermediates, such as those disclosed in the above mentioned U.S. Patents issued to Karpf et al., are directed to the preparation of a racemic mixture which is then resolved at a later step to isolate the desired isomer. Other methods are directed to an asymmetric synthesis of β-hydroxy ester by enantioselectively reducing the corresponding β-ketoester.

Moreover, in order to achieve a high yield of the desired product, some current asymmetric hydrogenation processes for reducing methyl 3-oxo-tetradecanoate require extremely pure reaction conditions, e.g., hydrogen gas purity of at least 99.99%, thus further increasing the cost of producing the corresponding β-hydroxy ester.

Therefore, there is a need for a process for producing δ-lactones. And there is a need for enantioselectively reducing β-ketoesters under conditions which do not require extremely pure reaction conditions or high hydrogen gas pressure.

SUMMARY OF THE INVENTION

One embodiment of the present invention provides a process for the preparation of a δ-lactone of the formula:

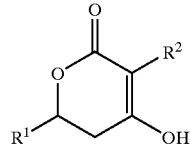

comprising:
(a) treating an acyl halide of the formula:

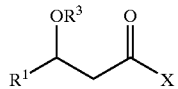

with a ketene acetal of the formula:

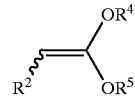

under conditions sufficient to produce a coupled intermediate product; and (b) providing conditions sufficient to produce the δ-lactone I from the coupled intermediate product, where $R^1$ is $C_1$–$C_{20}$ alkyl; $R^2$ is H or $C_1$–$C_{10}$ alkyl; $R^3$ is a hydroxy protecting group; each of $R^4$ and $R^5$ is independently $C_1$–$C_6$ alkyl, $C_5$–$C_{20}$ aryl, $C_6$–$C_{20}$ arylalkyl or —$SiR^8R^9R^{10}$; each of $R^8$, $R^9$, $R^{10}$ is independently $C_1$–$C_6$ alkyl or phenyl; and X is a halide.

The coupled product can be "trapped" (i.e., reacted) with a protecting group to produce an enol ether compound. Without being bound by any theory, it is believed that the coupled product or the enol ether compound is δ-hydroxy-β-enol ether ester or δ-hydroxy-protected-β-enol ether ester of the formula:

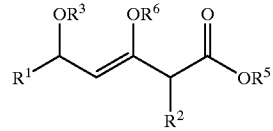

where $R^6$ is H or $R^4$, and $R^1$, $R^2$, $R^3$, $R^4$, and $R^5$ are those defined above. It should be appreciated that while Compound IV is depicted with the double bond in the β,γ-position, it can also exist with the double bond in the α,β-position. Moreover, the double bond can be either E- or Z-configuration. Thus, when referring to Compound IV, it is intended that these isomers, or mixtures thereof are also within the scope of the present invention.

Where $R^6$ of the coupled intermediate product (i.e., Compound IV) is not hydrogen (i.e., $R^6$ is a hydroxy protecting group), the step (b) above can include the steps of removing (i.e., deprotecting) $R^6$ or $R^3$ and $R^6$ to produce a deprotected intermediate, and contacting the deprotected intermediate with an acid under conditions sufficient to produce the δ-lactone I.

Another embodiment of the present invention provides a process for the preparation of the δ-lactone I comprising the steps of:

(a) treating an acyl halide of the formula:

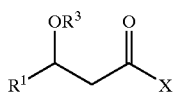
V with a malonate half acid of the formula:

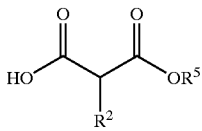
VI under conditions sufficient to produce a δ-hydroxy-β-ketoester of the formula:

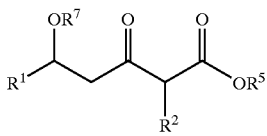
VII and (b) contacting the δ-hydroxy-protected-β-enol ether ester VI with an acid under conditions sufficient to produce the δ-lactone I, where $R^1$, $R^2$, $R^3$, $R^5$, and X are those described above, and $R^7$ is H or $R^3$.

Because Compound VII contains acidic group, it may exist in its enol (i.e., tautomeric) form under certain conditions. Thus, any reference to the Compound VII implicitly includes its tautomeric form.

Preferably, methods of the present invention provide an enantioselective synthesis of the δ-lactone I.

Another embodiment of the present invention provides a process for enantioselective preparation of a β-hydroxy ester of the formula:

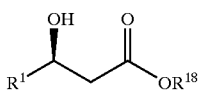
VIII comprising hydrogenating a β-ketoester of the formula:

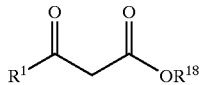
IX in the presence of about 40 bar of pressure or less of hydrogen gas and a ruthenium hydrogenation catalyst comprising a halide and a chiral substituted biphenyl phosphorous ligand, where $R^1$ is that described above, and $R^{18}$ is $C_1$–$C_6$ alkyl, $C_5$–$C_{20}$ aryl or $C_6$–$C_{20}$ arylalkyl.

Still another embodiment of the present invention provides compound selected from the group consisting of β-siloxy acyl halides of the formula:

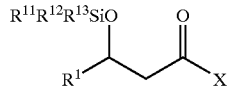
X

δ-siloxy-β-silyl enol ether esters of the formula:

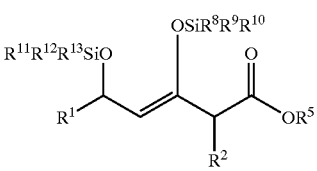
XI and δ-siloxy-β-ketoesters of the formula:

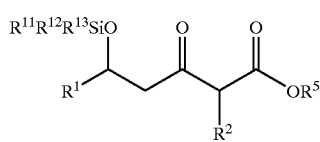
XII where $R^1$, $R^2$, $R^5$, $R^8$, $R^9$, $R^{10}$, and X are those described above, and each of $R^{11}$, $R^{12}$ and $R^{13}$ is independently $C_1$–$C_6$ alkyl or phenyl.

Similar to Compound IV, Compound XI can also exist in different olefin geometry (i.e., E- or Z- isomers) and/or different double bond location (i.e., in the α,β-position instead of in the β,γ-position as depicted). Thus, while Compound XI is depicted as that shown above, it is intended that the scope of the present invention includes these isomers of Compound XI.

DETAILED DESCRIPTION

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "alkyl" refers to aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, pentyl, hexyl, heptyl, octyl, decyl and undecyl.

The term "aryl" refers to monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl. Exemplary aryl groups include phenyl, toluyl, pyrrolyl, thiophenyl, furanyl, imidazolyl, pyrazolyl, 1,2,4-triazolyl, pyridinyl, pyrazinyl, pyrimidinyl, pyridazinyl, thiazolyl, isothiazolyl, oxazolyl, and isoxazolyl.

The present invention provides a process for the preparation of δ-lactones, such as 3,6-dialkyl-5,6-dihydro-4-hydroxy-2H-pyran-2-ones. In particular, the present invention provides a process for the preparation of a δ-lactone of the formula:

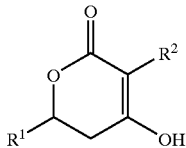

I where $R^1$ is $C_1$–$C_{20}$ alkyl, and $R^2$ is H or $C_1$–$C_{10}$ alkyl. In particular, the present invention provides a process for enantioselectively producing the δ-lactone I. In one specific embodiment of the present invention, the enantioselective process provides (R)-δ-lactone I having the following stereocenter:

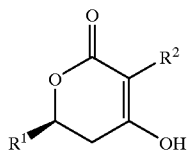

IA

It should be appreciated that the δ-lactone of formula I and the corresponding enantiomerically enriched δ-lactone IA may also exist in, or are in equilibrium with, their tautomeric forms:

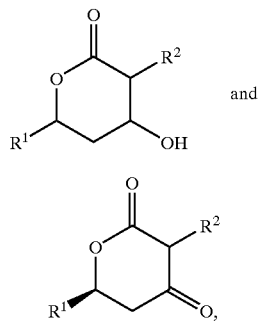

IB and

IC respectively. Therefore, any reference to the δ-lactone of formula I or IA implicitly includes its tautomeric form of formula IB or IC, respectively.

The present invention will now be described in reference to the synthesis of enantiomerically enriched δ-lactone IA. It should be appreciated that the racemic form of δ-lactone I or δ-lactone having the opposite stereochemical configuration as that of formula IA, while not explicitly discussed herein, can be readily prepared using the processes of the present invention by using a racemic mixture or opposite stereochemically configured starting materials, respectively.

In one embodiment of the process of the present invention, the process includes treating an acyl halide of the formula:

IIA with a ketene acetal of the formula:

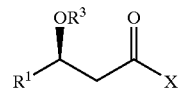

III under conditions sufficient to produce a δ-hydroxy-protected-β-enol ether ester of the formula:

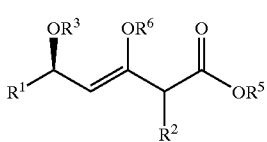

IVA where $R^1$ and $R^2$ are described above; $R^3$ is a hydroxy protecting group; each of $R^4$ and $R^5$ is independently $C_1$–$C_6$ alkyl, $C_5$–$C_{20}$ aryl (preferably $C_6$–$C_{20}$ aryl), $C_6$–$C_{20}$ arylalkyl (preferably $C_7$–$C_{20}$ arylalkyl) or a moiety of the formula —SiR$^8$R$^9$R$^{10}$; $R^6$ is H or $R^4$; X is halide, preferably chloride; and each of $R^8$, $R^9$ and $R^{10}$ is independently $C_1$–$C_6$ alkyl or phenyl.

A variety of protecting groups, including protecting groups for hydroxy and carboxylic acid functional groups, are known in the art, and can be employed. Examples of many of the possible protecting groups can be found in *Protective Groups in Organic Synthesis,* 3rd edition, T. W. Greene and P. G. M. Wuts, John Wiley & Sons, New York, 1999, which is incorporated herein by reference in its entirety.

With reference to compounds I–IVA above:

Preferably, $R^1$ is undecyl.

Preferably, $R^2$ is $C_1$–$C_{10}$ alkyl, more preferably hexyl.

Preferably, $R^3$ is a moiety of the formula —SiR$^{11}$R$^{12}$R$^{13}$, where each of $R^{11}$, $R^{12}$ and $R^{13}$ is independently $C_1$–$C_6$ alkyl or phenyl, more preferably each of $R^{11}$, $R^{12}$ and $R^{13}$ is independently methyl, isopropyl, tert-butyl or phenyl. More preferably $R^3$ is a moiety of the formula —Si(CH$_3$)$_3$.

Preferably, $R^4$ is a moiety of the formula —SiR$^8$R$^9$R$^{10}$. Preferably each of $R^8$, $R^9$ and $R^{10}$ is independently methyl, isopropyl, tert-butyl or phenyl. More preferably $R^4$ is a moiety of the formula —Si(CH$_3$)$_3$.

Preferably, $R^5$ is $C_1$–$C_6$ alkyl, $C_5$–$C_{20}$ aryl or $C_6$–$C_{20}$ arylalkyl. More preferably $R^5$ is $C_1$–$C_6$ alkyl. Still more preferably $R^5$ is methyl or ethyl.

Preferably, $R^6$ of compound V is same as $R^4$ of compound IV, particularly when $R^4$ is a moiety of the formula —SiR$^8$R$^9$R$^{10}$.

Processes of the present invention also include treating δ-hydroxy-protected-β-enol ether ester IVA under reaction conditions sufficient to remove at least one of the protecting groups (i.e., $R^6$ or $R^3$ and $R^6$) and contacting the resulting deprotected compound with an acid to produce the δ-lactone I.

A particularly useful ketene acetal III is a silyl ketene acetal in which $R^4$ is a moiety of the formula —SiR$^8$R$^9$R$^{10}$ and $R^5$ is $C_1$–$C_6$ alkyl, $C_5$–$C_{20}$ aryl or $C_6$–$C_{20}$ arylalkyl. Silyl ketenes can be readily prepared by any of the currently known methods. Some of the methods for preparing silyl ketenes are disclosed in Miura et al., *Bull. Chem. Soc. Jpn.*, 1991, 64, 1542–1553; Umemoto and Gotoh, *Bull Chem. Soc. Jpn.*, 1987, 60, 3823–3825; Sugimoto et al., *Chem. Lett.*, 1991, 1319–1322; Miura et al., *Bull. Chem. Soc. Jpn.*, 1992, 65, 1513–1521; and Shono et al., *J. Org. Chem.*, 1984, 49, 1056–1059, which are incorporated herein by reference in their entireties.

The silyl ketene acetal III can be prepared from the corresponding ester (i.e., a compound of the formula $R^2$—$CH_2$—$C(=O)OR^5$) by treating the ester with a strong base such as lithium hexamethyldisilazide (LiHMDS), a dialkylamide, e.g., lithium diisopropylamide and lithium tetramethylpiperidine (LiTMP), in a conventional aprotic organic solvent, such as tetrahydrofuran (THF), hexane, dimethoxy ethane (DME), ether or mixtures thereof, to generate an enolate and trapping (i.e., contacting) the enolate with a silylating agent, including a silyl triflate and silyl halide, such as silyl chloride, e.g., trimethylsilyl chloride. Dialkylamide can be prepared by treating the corresponding dialkylamine with a strong base, such as an alkyllithium (e.g., butyllithium) in a conventional aprotic organic solvent described above. The preparation of silyl ketene acetal III is generally carried out under preferably an inert atmosphere such as nitrogen, argon, or the like, at a temperature preferably at or less than about 0° C., more preferably at or less than about –30° C., and most preferably at about –78° C. The silyl ketene acetal III can be purified, e.g., by distillation under a reduced pressure. When $R^2$ is $C_1$–$C_{10}$ alkyl and $R^4$ and $R^5$ are different moieties, the resulting silyl ketene acetal III can have two different geometric isomers, i.e., E- or Z-double bond configuration. It should be appreciated that since the carbon atom of δ-lactone I containing $R^2$ group can be readily isomerized, the geometric isomer of the silyl ketene acetal III is not important for enantioselective processes of the present invention.

In one particular embodiment of the present invention, the δ-hydroxy-protected-β-enol ether ester IVA, where $R^6$ is $R^4$, is prepared by reacting the above described silyl ketene acetal III with the acyl halide IIA, where $R^3$ is a moiety of the formula —$SiR^{11}R^{12}R^{13}$. The reaction is typically carried out in a conventional aprotic organic solvent, such as THF, toluene, heptane, hexane or mixtures thereof, in the presence of a tertiary amine including trialkylamine, such as triethylamine or tributylamine, under preferably an inert atmosphere described above. Preferably, the reaction temperature is in the range of from about 0° C. to about 25° C.

The crude δ-hydroxy-protected-β-enol ether ester IVA can be purified, e.g., by distillation under a reduced pressure or by chromatography, or it can be used directly in the next step without any purification. As used herein, a "crude" compound refers to a compound which is not subject to a separate purification step other than a conventional work-up of the reaction.

The resulting δ-hydroxy-protected-β-enol ether ester IVA, in particular where $R^3$ and $R^6$ are a moiety of the formula —$SiR^{11}R^{12}R^{13}$ and —$SiR^8R^9R^{10}$, respectively, can be selectively monodesilylated to produce a δ-siloxy-β-ketoester of the formula:

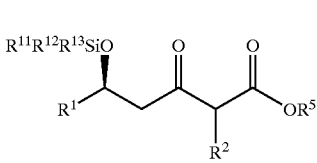

under acidic or basic conditions, preferably under basic conditions. For basic monodesilylation conditions, typically a tertiary amine including a trialkylamine, such as triethylamine or preferably tributylamine; or a bicarbonate, such as potassium bicarbonate, lithium bicarbonate or preferably sodium bicarbonate, is used. The monodesilylation reaction can be conducted in a protic solvent, such as alkyl alcohol (e.g., methanol, ethanol and isopropanol), or a mixture of aprotic organic solvent and a protic solvent (e.g., alkyl alcohol or water). Exemplary aprotic organic solvents which are useful in monodesilylation reaction include methylene chloride, dimethyl formamide (DMF), dimethyl sulfoxide (DMSO), THF and ethyl ether. Preferably, the monodesilylation reaction is carried out in an alkyl alcohol solvent, more preferably in methanol. The monodesilylation reaction temperature range is preferably from about 0° C. to about 25° C.

The δ-siloxy-β-ketoester VIA can be further desilylated under acidic or basic conditions, preferably under acidic conditions, and cyclized to produce the δ-lactone I. Desilylation of a hydroxy group is well known to one of ordinary skill in the art and is disclosed in the above mentioned *Protective Groups in Organic Synthesis*. For acidic desilylation conditions, typically an acid such as hydrochloric acid, sulfuric acid, phosphoric acid, acetic acid, or trifluoroacetic acid is used. Desilylation of the δ-siloxy-β-ketoester VIA under an acidic condition results in a rapid cyclization to produce the δ-lactone I, thus eliminating a need for a separate cyclization step.

Alternatively, the δ-lactone I can be produced by removing both of the protecting groups ($R^3$ and $R^6$) from the δ-hydroxy-protected-β-enol ether ester IVA in a single step and contacting the deprotected product with an acid under conditions sufficient to produce the δ-lactone I. As used herein, the term "single step" refers to removal of both protecting groups $R^3$ and $R^6$ under same reaction conditions. In a particular embodiment of the present invention, where $R^3$ and $R^6$ of δ-hydroxy-protected-β-enol ether ester IVA are moieties of the formula —$SiR^{11}R^{12}R^{13}$ and —$SiR^8R^9R^{10}$, respectively, it is preferred that both of the silyl groups are removed in a single step under a basic condition, typically using a hydroxide or preferably a carbonate. Exemplary hydroxides which can be used in the present invention include sodium hydroxide, potassium hydroxide, lithium hydroxide, calcium hydroxide and magnesium hydroxide. Exemplary carbonates which are useful in the present invention include potassium carbonate, lithium carbonate, sodium carbonate and cesium carbonate. Preferred carbonate is potassium carbonate. A single step removal of both silyl groups can be carried out in a same solvent as those described above for monodesilylation. The reaction temperature range of a single step desilylation and subsequent production of the δ-lactone I is preferably from about 0° C. to about 25° C.

Typically, the δ-lactone I is produced by adjusting the pH of the reaction mixture to from about pH 3 to about pH 5. Any acid which is capable of providing the above described pH range of the reaction mixture may be used, such acids include, but are not limited to, hydrochloric acid, sulfuric acid, and phosphoric acid. In one particular embodiment of the present invention, hydrochloric acid is used to produce the δ-lactone. The δ-lactone I thus formed typically precipitates from the reaction mixture, e.g., when methanol is used as the solvent. The δ-lactone I can be further purified, e.g., by recrystallization, to obtain higher purity and/or higher enantiomeric excess of δ-lactone I.

In another embodiment of the present invention, the acyl halide IIA is treated with a malonate half acid of the formula:

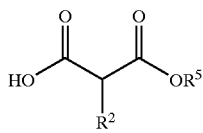
V under conditions sufficient to produce a δ-hydroxy-β-ketoester of the formula:

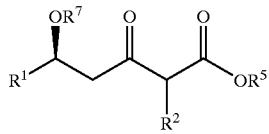
VIA where $R^1$, $R^2$ and $R^5$ are described above, and $R^7$ is H or $R^3$. Preferably, $R^7$ is H.

The process of the present invention also includes contacting the δ-hydroxy-β-ketoester VIA with a base or preferably an acid under conditions sufficient to produce the δ-lactone I, as described above.

The reaction between the acyl halide IIA and the malonate half acid V is typically carried out in the presence of a metal coordinating agent and a tertiary amine base. See for example, Rathke and Cowan, *J. Org. Chem.*, 1985, 50, 2622–2624, and Clay et al., *Synthesis*, 1993, 290–292, which are incorporated herein by reference in their entirety. The reaction can be conducted under an aprotic organic solvent, such as n-butyl ether, THF, acetonitrile, methylene chloride, dimethoxyethane (DME), methyl t-butyl ether (MTBE), toluene, 2-methyltetrahydrofuran (2-Me—THF), with THF being the preferred solvent. Without being bound by any theory, it is believed that the use of a metal coordinating agent generates a metal enolate of the malonate half acid V, which is sufficiently reactive to react with the acyl halide IIA, but is not basic enough to deprotonate the initially formed product, which contains an acidic proton.

In general, the reaction between the acyl halide IIA and the malonate half acid V is conducted by adding the acyl halide IIA, preferably in a solution, to a solution mixture which includes the malonate half acid V, the metal coordinating agent and the tertiary amine base. Higher yield of the δ-hydroxy-β-ketoester VIA can be obtained by using at least about 2 equiv. of a relatively non-nucleophilic base, such as a tertiary amine, and at least 1 equiv. of the metal coordinating agent relative to the amount of malonate half acid V.

Exemplary metal coordinating agents include magnesium salts including magnesium halides, such as $MgCl_2$, $MgBr_2$ and $MgI_2$; manganese salts, such as manganese halides and manganese acetates; lithium salts, such as lithium halides; samarium salts, such as samarium halides; and mixtures of sodium and lithium salts, such as mixtures of sodium halides and lithium halides. Preferably, the metal coordinating agent is a magnesium salt, more preferably magnesium chloride.

Exemplary tertiary amine bases which are useful in the present invention include trialkylamines, such as triethylamine, diethylisopropylamine and tributylamine. Preferably, the tertiary amine base is a trialkylamine, more preferably triethylamine, diethylisopropylamine or tributylamine.

Typically, the reaction between the acyl halide IIA and the malonate half acid V is conducted at a temperature ranging from about 0° C. to about 35° C., under preferably an inert atmosphere as those described above. Preferably, the reaction is conducted at about 25° C.

The resulting δ-hydroxy-β-ketoester VIA can be isolated or preferably used directly without isolation and treated with an acid under conditions sufficient to produce the δ-lactone I. For example, after reacting the acyl halide IIA with the malonate half acid V, an acid described above is added to the resulting reaction mixture, which results in the formation of the δ-lactone I.

Preferably, alkyl malonate half acid V is methyl or ethyl malonate half acid V, where $R^5$ is methyl or ethyl, as the methyl or ethyl δ-hydroxy-β-ketoester VIA produces the δ-lactone I in higher yield than other malonate half acid V under similar reaction conditions and time. One can take advantage of this higher yield by methyl or ethyl malonate half acid V by converting a non-methyl or non-ethyl malonate half acid V to methyl or methyl malonate half acid V, and then reacting the methyl or ethyl malonate half acid V with the acyl halide IIA to produce the δ-lactone I. For example, propyl malonate half acid V, where $R^5$ is propyl, can be reacted with a metal methoxide, such as sodium methoxide, in methanol under conditions sufficient to produce the methyl malonate half acid V from propyl malonate half acid V, and then reacting the resulting methyl malonate half acid V with acyl halide IIA to produce the δ-lactone I. Alternatively, the product of a reaction between non-methyl malonate half acid V and the acyl halide IIA can be converted to its corresponding methyl δ-hydroxy-β-ketoester VIA prior to contacting with an acid or preferably in situ during the cyclization step to produce the δ-lactone I.

The malonate half acid V, where $R^2$ is not H, can be prepared by a variety of methods. For example, malonate half acid V can be prepared by treating malonate diester, e.g., $R^5OC(=O)CH_2C(=O)OR^5$, with a base, such as sodium ethoxide, to generate the corresponding enolate and contacting the enolate with an alkyl group containing a leaving group, for example, mesylate, tosylate and halides such as bromide and iodide, to produce an alkyl malonate diester, i.e., $R^5OC(=O)CH(R^2)C(=O)OR^5$. The alkyl malonate diester is then monosaponified, typically using less than about 1 equiv., preferably about 0.9 equiv. of hydroxide in the corresponding $R^5$ alcohol solvent to produce the malonate half acid V, for example, by treating with a hydroxide, such as potassium hydroxide, sodium hydroxide or lithium hydroxide, in methanol (when $R^5$ is methyl) or ethanol (when $R^5$ is ethyl).

Processes of the present invention can also include the step of producing the acyl halide IIA from a β-hydroxy acid or salts thereof, such as potassium or sodium salts, of the formula:

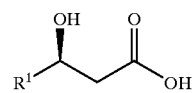
XIII by protecting the hydroxy group to produce a β-hydroxy-protected ester of the formula:

XIV

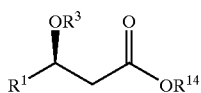

and contacting the β-hydroxy-protected ester XIV with an acyl halogenating agent under conditions sufficient to produce the acyl halide IIA, where $R^1$ and $R^3$ are described above and $R^{14}$ is H, $R^3$ or a carboxylate counter cation. As used herein, the term "carboxylate counter cation" refers to a counter ion of the carboxylic salt of formula XIV. Exemplary carboxylate counter cations include metal cations, such as sodium, lithium and potassium; ammonium; mono-, di-, tri- and tetraalkylammonium; pyridinium; and other suitable cations for carboxylic anions which are known to one of ordinary skill in the art.

In one particular embodiment of the present invention, the acyl halide IIA is produced by contacting the β-hydroxy acid XIII with a silylating agent to produce a β-silyloxy silyl ester of the formula:

XV

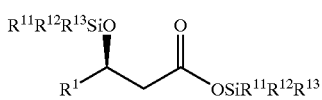

and contacting the β-silyloxy silyl ester XV with an acyl halogenating agent, where $R^{11}$, $R^{12}$ and $R^{13}$ are those described above. Any hydroxy silylating agent known in the art can be used to produce the β-silyloxy silyl ester XV. Exemplary silylating agents include compounds of the formula $X^1$—$SiR^{11}R^{12}R^{13}$, where $R^{11}$, $R^{12}$ and $R^{13}$ are described above and $X^1$ is a halide or triflate; and hexamethyldisilazane (when $R^{11}$, $R^{12}$ and $R^{13}$ are methyl).

For example, β-trimethylsiloxy trimethyl silyl ester of compound XV, where $R^{11}$, $R^{12}$ and $R^{13}$ are methyl, can be prepared by treating the β-hydroxy acid with chlorotrimethylsilane (TMSCl) in the presence of pyridine preferably under an inert atmosphere described above. The reaction is preferable conducted in an aprotic organic solvent such as methylene chloride, MTBE, toluene and THF, with THF being a particularly preferred solvent. The temperature range of the reaction is generally from about 0° C. to about 25° C., preferably the reaction temperature is about 25° C. The reaction can also include 4-dimethylaminopyridine (DMAP) or other silylating catalyst known to one of ordinary skill in the art. When a silylating catalyst such as DMAP is present, it is typically used at about 1 mole %. Even without the presence of a silylating catalyst, silylation is typically complete within few hours, generally within about 2 hours at room temperature.

Alternatively, the β-trimethylsiloxy trimethyl silyl ester XV can be prepared by using hexamethyldisilazane (HMDS). For example, heating a mixture of β-hydroxy acid XIII and HMDS in an aprotic organic solvent, such as toluene or preferably THF, produces the β-trimethylsiloxy trimethyl silyl ester XV. When HMDS is used, one of the by-products of the reaction is ammonia, which can be readily removed by partially distilling the reaction solvent typically at atmospheric pressure. The resulting partially concentrated solution of β-trimethylsiloxy trimethyl silyl ester XV can be used directly in the acyl halide IIA producing step without further purification.

A variety of acyl halogenating agents are known to one of ordinary skill in the art. Exemplary acyl halogenating agents and general procedures for using the same are disclosed, for example, in "Comprehensive Organic Synthesis," vol. 6, Trost, Fleming and Winterfeldt eds., Pergamon Press, 1991, pp. 301–319, and "The Chemistry of Acyl Halides," Patai, ed., Interscience Publishers, 1972, pp. 35–64, which are incorporated herein by reference in their entireties. It has been found by the present inventors that β-hydroxy-protected ester XIV, in particular β-trimethylsiloxy trimethyl silyl ester XV, can be readily converted to the acyl halide IIA using oxalyl chloride or thionyl chloride in an aprotic organic solvent, such as toluene or preferably THF.

When using oxalyl chloride as the acyl halogenating agent, pyridine and a catalytic amount of silylating catalyst such as DMF is typically used. However, when thionyl chloride is used as the acyl halogenating agent in place of oxalyl chloride, a need for using a silylating catalyst such as DMF is eliminated. In either case, formation of pyridinium salts in an acyl halogenation reaction may complicate the reaction between the ketene acetal III and the acyl halide IIA. To avoid possible complications in the reaction between the ketene acetal III and the acyl halide IIA, typically pyridinium salts are removed from the reaction mixture, e.g., by filtration. The resulting reaction mixture is then further concentrated, e.g., by distillation, which also removes at least a portion of any residual TMSCl, thionyl chloride and THF. The distillation is generally conducted under a reduced pressure at about 0° C.

It has been found by the present inventors that when HMDS is used as the silylating agent for β-hydroxy acid XIII in THF, the subsequent acyl halogenation reaction with thionyl chloride in THF is slow at 0° C. and gives poor yields at higher reaction temperatures. However, a presence of pyridinium salts, such as pyridinium hydrochloride, pyridine or DMAP increases the reaction rate and yields higher amounts of the desired acyl halide IIA. Thus, when HMDS is used as the silylating agent, pyridine is typically added to the subsequent acyl halogenation reaction. The amount of pyridine added is generally from about 1 mole % to about 10 mole %, and preferably about 2 mole %. The halogenation reaction is conducted at a reaction temperature of typically about 0° C.

Processes of the present invention can also include enantioselective preparation of β-hydroxy acid XIII from a β-ketoester of the formula:

XVI

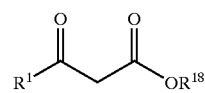

by enantioselectively reducing the ketone carbonyl of the β-ketoester XVI and saponifying the ester group to produce the β-hydroxy acid XIII, where $R^1$ is described above and $R^{18}$ is $C_1$–$C_6$ alkyl, $C_5$–$C_{20}$ aryl or $C_6$–$C_{20}$ arylalkyl. Preferably $R^{18}$ is $C_1$–$C_6$ alkyl, more preferably methyl or ethyl.

In one particular embodiment of the present invention, an enantioselective preparation of β-hydroxy ester XIII involves hydrogenation of the β-ketoester XVI in the presence of a chiral hydrogenation catalyst. It should be appreciated that an achiral hydrogenation catalyst will result in racemic mixture of β-hydroxy ester XIII, and a chiral hydrogenation catalyst having an opposite configuration as those described below will result in β-hydroxy ester having an opposite configuration as that shown in Figure XIII. Specifically, the present invention provides a process for enantioselectively reducing the β-ketoester XVI using an enantiomerically enriched hydrogenation catalyst, i.e., hydrogenation catalyst having greater than about 97% enantiomeric excess (%ee).

In one particular embodiment of the present invention, the chiral hydrogenation catalyst comprises a ruthenium catalyst containing a chiral ligand such as those shown in the Examples section, including a catalyst of the formula:

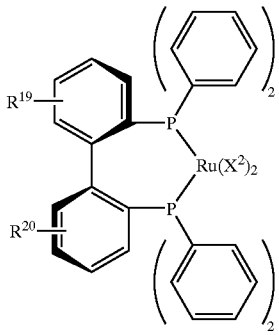

where $X^2$ is a halide, such as iodide, bromide or preferably chloride, and each of $R^{19}$ and $R^{20}$ is independently H, $C_1$–$C_6$ alkyl or $C_1$–$C_6$ alkoxy, provided at least one of $R^{19}$ or $R^{20}$ is not H. Moreover, each phenyl group may contain more than one $R^{19}$ or $R^{20}$ groups. Furthermore, one or both of the phenyl groups of the biphenyl moiety may be replaced with other aromatic groups such as a naphthyl, pyridyl or other substituted aryl groups.

One of the useful hydrogenation catalysts of the present invention is a product produced by contacting a ruthenium diacetate of the formula $Ru(OAc)_2((R)\text{-MeOBIPHEP})$ with a halide source, such as alkaline metal halides (e.g., LiX, NaX, KX and CsX, where X is a halide) or hydrohalides (e.g., HX, where X is a halide), preferably hydrochloric acid, where $Ru(OAc)_2((R)\text{-MeOBIPHEP})$ is a compound of the formula:

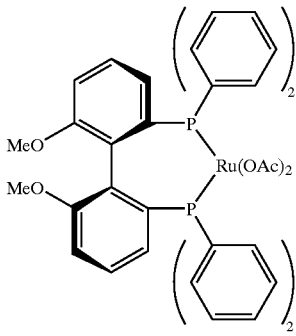

Without being bound by any theory, it is believed that treating $Ru(OAc)_2((R)\text{-MeOBIPHEP})$ with hydrochloric acid results in replacing both of the OAc groups with chloride; thus, the resulting product is believed to be $Ru(Cl)_2((R)\text{-MeOBIPHEP})$. Interestingly, however, when $Ru(OAc)_2((R)\text{-MeOBIPHEP})$ is treated with less than about 2 equiv. of HCl, the resulting hydrogenation catalyst does not produce (R)-3-hydroxy ester XIII in a high enantiomeric excess. Surprisingly and unexpectedly, in some cases such a hydrogenation catalyst produces (S)-3-hydroxy ester predominantly. However, when at least about 5 equiv. of HCl is added to $Ru(OAc)_2((R)\text{-MeOBIPHEP})$, preferably at least about 10 equiv. and more preferably at least about 20 equiv., the resulting hydrogenation catalyst enantioselectively reduces the β-ketoester XVI to the corresponding (3R)-3-hydroxy ester.

The precursor of chiral hydrogenation catalyst of the present invention, i.e., ruthenium dicarboxylate diphosphine compound or $[Ru(OC(=O)R')_2(diphosphine)]$, can be prepared according to the following reaction scheme:

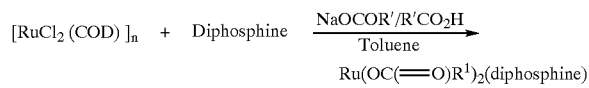

In this manner a variety of chiral ruthenium dicarboxylate diphosphines, including those listed in Example 16, can be prepared. The process for preparing a ruthenium dicarboxylate diphosphine compound generally involves contacting $[RuCl_2(COD)]_n$, which is commercially available or preferably prepared according to the procedure of Albers et al., Inorg. Synth., 1989, 26, 68, with a mixture of a carboxylate salt and the corresponding carboxylic acid, i.e., $MOC(=O)R'$ and $HOC(=O)R'$ mixture, such as sodium acetate/acetic acid and sodium pivalate/pivalic acid mixtures, in an aprotic organic solvent, preferably toluene. The mixture is heated at a temperature of about 80° C. to about 120° C., preferably about 100° C. A typical reaction time is from about 15 hours to about 72 hours, preferably from about 20 hours to about 48 hours. The amount of carboxylate salt used can be about 2 equiv. to about 50 equiv., preferably about 2 equiv. to about 25 equiv., more preferably about 2.1 equiv. to about 10 equiv., and most preferably about 2.5 equiv. Preferably a small excess of $[RuCl_2(COD)]_n$ is used relative to the diphosphine compound to ensure complete conversion of the diphosphine compound.

While commercially available $[RuCl_2(COD)]_n$ complex can be used, it has been found that freshly prepared $[RuCl_2(COD)]_n$ complex from ruthenium trichloride generally affords shorter reaction time, more consistant and/or higher yield of ruthenium dicarboxylate diphosphine compound. In this manner, a one-pot synthesis of ruthenium dicarboxylate diphosphine compound can be achieved from relatively inexpensive and readily available ruthenium trichloride.

The β-hydroxy compound (e.g., 3-(R)-hydroxy compound) XIII can be further purified, i.e., enantiomerically enriched, by recrystallizing the initial product to afford a product having at least about 99 %ee. Therefore, it should be appreciated that depending on the cost of a particular chiral hydrogenation catalyst, it may be more economical to use a chiral hydrogenation catalyst which provides less than about 95 %ee of the β-hydroxy compound XIII, which can be further enantiomerically enriched by recrystallization.

Unlike currently used ruthenium-based hydrogenation catalysts for asymmetric reduction of methyl 3-oxotetradecano-ate, the hydrogenation catalyst of the present invention does not require high purity conditions, e.g., hydrogen gas having purity of at least about 99.99%, to produce methyl 3-hydroxytetradecanoate in high yield and high enantiomeric excess. In fact, the asymmetric hydrogenation of methyl 3-oxotetradecanoate under technical grade conditions, e.g., hydrogen gas having purity of about 99.5% and nitrogen gas having purity of about 99.5%, using the hydrogenation catalyst of the present invention proceeds with a substantially similar rate as those requiring high purity reaction conditions. Moreover, the hydrogenation catalyst of the present invention allows the use of lower hydrogen gas pressure, thereby reducing the cost of initial capital investments and reducing the danger associated with high hydrogen gas pressure reaction conditions. In addition, by using asymmetric hydrogenation processes described above, the present invention allows asymmetric synthesis of the δ-lactone I without a need for resolving any racemic intermediates.

Typically, hydrogenation of β-ketoester XVI, e.g., methyl 3-oxotetradecanoate, is conducted in a conventional hydrogenation solvent including an alkyl alcohol, such as ethanol or preferably in methanol, at a reaction temperature of about 80° C. The concentration of the substrate (i.e., β-ketoester XVI) in hydrogenation reaction is generally at about 40 wt %, and the ratio of HCl to Ru(OAc)$_2$((R)-MeOBIPHEP) in the hydrogenation catalyst is about 20:1. A typical ratio of methyl 3-oxotetradecanoate to the hydrogenation catalyst is about 50,000:1. To this reaction mixture, typically about 40 bar of technical grade hydrogen gas is added, and the reaction is allowed to proceed for about 4 hours (h). The resulting methyl (R)-3-hydroxy tetradecanoate is then saponified by diluting the crude hydrogenation solution in methanol and 28% aqueous sodium hydroxide solution at room temperature. The saponified product is then acidified with an acid, such as sulfuric acid, to isolate (R)-3-hydroxy tetradecanoic acid. In this manner, the β-hydroxy acid IIA, such as (R)-3-hydroxy tetradecanoic acid, can be produced in at least about 90% isolated yield from the corresponding β-ketoester XVI, more preferably in at least about 93% isolated yield and most preferably in at least about 95% isolated yield. The enantiomeric excess of the product is at least about 90%ee, preferably at least about 95%ee, and more preferably at least about 99%ee. The enantiomeric excess can be increased to at least about 95%ee after a single recrystallization, preferably at least about 99%ee, and most preferably at least about 99.5%ee.

The β-ketoester XVI can be readily prepared by a variety of known methods. See for example, Case-Green, *Synlett*, 1991, 781–782 and U.S. Pat. No. 5,945,559, issued to Sotoguchi et al., which are incorporated by reference herein in their entireties.

The δ-lactone I can also be prepared by treating a 2-alkyl-acetoacetate ester of the formula:

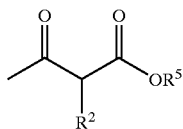

XVII with acyl halide IIA and contacting the resulting product with a base or preferably an acid, such as those described above, under conditions sufficient to produce the δ-lactone I, wherein $R^2$ and $R^5$ are those described above.

Without being bound by any theory, it is believed that a reaction between the 2-alkyl-acetoacetate ester XVII and the acyl halide IIA produces α-acetyl-β-ketoester of the formula:

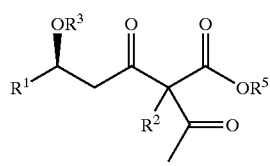

XVIII as the initial product, where $R^1$, $R^3$ and $R^5$ are those described above and $R^2$ is $C_1$–$C_{10}$ alkyl. Solvolysis, e.g., methanolysis (i.e., contacting with methanol), in basic or preferably acidic conditions, of α-acetyl-β-ketoester XVIII removes the acyl group to produce the δ-hydroxy-β-ketoester VIA, where $R^7$ is $R^3$, which can then be used to produce the δ-lactone I as described above. Preparation of β-ketoesters from methyl acetoacetate is disclosed in Japanese Patent No. 10-53561, issued to Sotokuchi et al., which is incorporated by reference herein in its entirety.

The 2-alkyl-acetoacetate ester XVII can be prepared by forming an enolate of acetoacetate ester by contacting the acetoacetate ester with a base, such as calcium oxide or calcium hydroxide, in typically refluxing toluene followed by reacting the enolate with the acyl halide IIA.

Alternatively, the δ-hydroxy-β-ketoester VIA (where $R^2$ is $C_1$–$C_{10}$ alkyl, preferably hexyl), and hence ultimately the δ-lactone I, can be produced by reacting acetoacetate ester (compound XVII, where $R^2$ is H) with acyl chloride IIA as described above to initially produce the δ-hydroxy-β-ketoester VIA (where $R^2$ is H). The δ-hydroxy-β-ketoester VIA, where $R^2$ is H, can be deprotonated with a base to produce a second enolate which can be reacted with an alkyl group containing a leaving group, such as those described above, e.g., hexyl bromide, to produce the δ-hydroxy-β-ketoester VIA (where $R^2$ is $C_1$–$C_{10}$ alkyl, e.g., hexyl). In generating the second enolate, a reverse addition, i.e., addition of the δ-hydroxy-β-ketoester VIA (where $R^2$ is H) to a solution containing a base, can be used, for example, to reduce the amount of elimination product which may result in the conventional addition step, i.e., addition of a base to a solution of the δ-hydroxy-β-ketoester VIA.

Additional objects, advantages, and novel features of this invention will become apparent to those skilled in the art upon examination of the following examples thereof, which are not intended to be limiting.

EXAMPLES

Example 1

This example illustrates a method for preparing 1-methoxy-1-trimethylsiloxy-1-octene.

A 1000-mL, 3-necked flask was fitted with Claisen adapter with septum/thermocouple and nitrogen adapter, paddle stirrer, and 250-mL pressure-equilibrating addition funnel. The flask was sealed and the atmosphere changed to dry nitrogen (10 nitrogen-vacuum cycles). Dry THF (100 mL) and 69.9 mL (50.5 g, 499 mmol, 1.05 equiv) of diisopropylamine were added via syringe. The solution was cooled to −10° C., and 190 mL of 2.5 M butyllithium in hexane (475 mmol) was added dropwise via syringe over 28 min at 0 to −5° C. The addition funnel was rinsed with 10 mL of dry hexane. The resulting solution was stirred at 0 to −5° C. for 30 min then cooled to −78° C. Methyl octanoate (85.7 mL, 75.16 g, 475 mmol) was added via syringe to the addition funnel then added dropwise to the reaction mixture at −75° C. to −78° C. over 70 min. The resulting mixture was stirred at −78° C. for 30 min. The addition funnel is rinsed with 10 mL dry hexane. Chlorotrimethylsilane (TMSCl) (72 mL, 61.9 g, 570 mmol, 1.2 equiv) was added via syringe to the addition funnel then added dropwise to the reaction mixture at −75° C. to −78° C. over 50 min. The addition funnel was rinsed with 10 mL dry hexane. The suspension was stirred at −75° C. to −78° C. for 30 min and then allowed to warm to 25° C. over 60 min and stir for 30 min.

The reaction mixture was concentrated on a rotary evaporator at 25–30° C. and 40–100 mm Hg. The residue was diluted with 200 mL dry heptane then suction filtered under nitrogen (using a Teflon™ cannula and 60-mL airlessware funnel with medium frit). The flask, funnel and solids were rinsed with 100 mL of dry heptane. The combined mother liquors were concentrated on a rotary evaporator at 25–30° C. and 10–90 mm Hg to afford 119.2 g of pale yellow oil. The oil was distilled using a short-path apparatus at 1.0–1.2 nun Hg (b.p. 82–84° C.) to afford 99.86 g of clear colorless liquid.

Example 2

This example illustrates a method for preparing (R)-3-hydroxytetradecanoic acid.

A solution of 33.67 g (600 mmol) potassium hydroxide in 600 mL of $H_2O$ was added dropwise at 0–5° C. to a solution of 60.00 g (232.8 mmol) of the methyl (R)-3-hydroxytetradecanoate in 1200 mL of ethanol over 80 min. The resulting suspension was stirred at 0° C. for 3 h. Hydrochloric acid (1 N, 600 mL, 600 mmol) was then added dropwise at 0–5° C. over 50 min. The resulting suspension was stirred at 0° C. for 15 min. The precipitate was suction filtered, slurry-washed with 600 mL of $H_2O$, then air dried at 25° C. for 64 h to afford 52.76 g of colorless solid. The solid was recrystallized from 400 mL of ethyl ether (hot filter and cooled to −28° C.) to afford 49.87 g (87.9%) of colorless solid after −2 h of air drying and 2 h of drying in vacuo at 25° C.

Example 3

This example illustrates a method for preparing trimethylsilyl (R)-3-(trimethylsiloxy)tetradecanoate.

A 1000-mL, 3-necked flask was fitted with Claisen adapter with septum/thermocouple and nitrogen adapter, paddle stirrer, and 50-mL pressure-equilibrating addition funnel with septum. The flask was charged with 45.00 g (184.1 mmol) of (R)-3-hydroxytetradecanoic acid and DMAP (113 mg, 0.921 mmol, 0.5 mol %). The reactor was sealed, nitrogen started, then 200 mL of dry THF and 30.8 mL (30.12 g, 380.8 mmol) of dry pyridine were added via syringe. Stirring (200 rpm) was started and the flask was immersed in a cool water bath. The addition funnel was charged with 49.0 mL (41.91 g, 385.8 mmol) of TMSCl. The TMSCl was then added dropwise at 20–25° C. over 30 min. The addition funnel was rinsed with 5 mL of dry THF. The suspension was stirred at 20–25° C. for 20 h then used directly in the next step.

300 MHz $^1H$ NMR (CDCl$_3$) δ 0.11 (s, 9H), 0.27 (s, 9H), 0.87 (t, 3H), 1.22–1.37 (m, 18H), 1.42–1.49 (m, 2H), 2.41–2.44 (d, 2H), 4.08 (m, 1H).

NMR analysis of another run indicated complete conversion in 2 h and no change at 20 h.

Example 4

This example illustrates a method for preparing (R)-3-(trimethylsiloxy)tetradecanoyl chloride.

The suspension of trimethylsilyl (R)-3-(trimethylsiloxy)-tetradecanoate was cooled to 0° C. and 0.14 mL (135 mg, 1.84 numol, 1.0 mol %) of dry DMF was added via syringe. The addition funnel was charged with thionyl chloride (17.5 mL, 28.5 g, 240 mmol, 1.3 equiv) which was then added dropwise at 0 to −5° C. over 11 min. The resulting suspension was stirred at −2 to −3° C. for 7 h.

Concentration of the reaction mixture at 0° C. and 30 mm Hg on a rotary evaporator (dry ice-methanol condenser) resulted in recovery of a THF/TMSCl mixture (163 mL colorless liquid). The residue was diluted with 150 mL of dry hexane at 0° C. The suspension was filtered under dry nitrogen (Teflon™ cannula and 200-mL airlessware funnel). The flask and solids were rinsed with 100 mL of dry hexane at 0° C. The combined mother liquors were concentrated at 0° C. and 30 mm Hg on a rotary evaporator (dry ice-methanol condenser) (254 mL colorless liquid with some solids). The residual oil was used directly in the next step.

300 MHz $^1H$ NMR (CDCl$_3$) δ 0.12 (s, 9H), 0.88 (t, 3H), 1.22–1.37 (m 18H), 1.42–1.52 (m, 2H), 2.95 (d, 2H), 4.18 (m, 1H).

Example 5

This example illustrates a method for preparing methyl (R)-3,5-bis-Trimethylsiloxy)-2-hexyl-3-hexadecenoate.

A 1000-mL flask was fitted with Claisen adapter with septum/thermocouple and nitrogen adapter, paddle stirrer, and a 50-mL pressure-equilibrating addition funnel. The flask was sealed and nitrogen flow and stirring (200 rpm) were started. The crude (R)-3-(trimethylsiloxy) tetradecanoyl chloride of Example 4 was slowly diluted with 150 mL of dry THF at 0 to −5° C. Distilled 1-methoxy-1-trimethylsiloxy-1-octene (50.2 mL, 42.42 g, ~184 mmol) from Example 1 was added via syringe. The addition funnel was charged with 25.7 mL (18.63 g, 184.1 mmol) of triethylamine. The amine was then added dropwise at −10 to 0° C. over 20 min. The addition funnel was rinsed with 5 mL of dry THF. The resulting suspension was stirred at −5° C. for 16 h.

The suspension was concentrated on a rotary evaporator at 25–30° C. and 30–80 mm Hg (150 mL of colorless liquid with some solid). The residue was diluted with 200 mL of dry hexane and the suspension stirred briefly at 25° C. The suspension was suction filtered through 10 g of celite under dry nitrogen (Teflon™ cannula and 200-mL airlessware funnel). The flask and cake were rinsed with 100 mL of dry hexane. The mother liquors were concentrated on a rotary evaporator at 25–30° C. and 30–80 mm Hg to afford 94.78 g of slightly cloudy orange oil, which was used directly in the next step.

Methyl (R)-3,5-bis-(Trimethylsiloxy)-2-hexyl-3-hexadecenoate:

300 MHz $^1H$ NMR (CDCl$_3$) δ 0.08 (d, 9H), 0.19 (d, 9H), 0.87 (m, 6H), 1.28–1.58 (m, 30H), 2.86–2.91 (m, 1H), 3.75 (d, 3H), 4.33–4.42 (m, 1H), 4.65 (t, 1H).

Methyl (3R)-2-hexyl-5-oxo-3-(trimethylsiloxy) hexadecanoate:

300 MHz $^1H$ NMR (CDCl$_3$) δ 0.06 (d, 9H), 0.81–0.89 (m, 6H), 1.16–1.46 (m, 28H), 174–1.86 (m, 2H), 2.46–2.76 (m, 2H), 3.38–3.46 (m, 1H), 3.69 (m, 3H), 4.09–4.19 (broad m, 1H).

NMR analysis of another run indicated complete conversion in about 2 h and no significant change after 16 h.

Example 6

This example illustrates a method for preparing (R)-3-hexyl-4-hydroxy-6-undecyl-5,6-dihydropyran-2-one.

A 1000-mL flask was fitted with septum/thermocouple, paddle stirrer, and a nitrogen adapter. The flask was sealed and nitrogen flow and stirring (200 rpm) started. The crude methyl (R)-3,5-bis-(trimethylsiloxy)-2-hexyl-3-hexadecenoate of Example 5 was cooled to 0° C. and anhydrous potassium carbonate powder (38.16 g, 276 mmol) and 350 mL of cold methanol were added at 0 to 5° C. The suspension was stirred at 0° C. for 17 h.

Hydrochloric acid (46 mL of 12 N) was added dropwise at 0 to 5° C. over 43 min. The suspension was diluted with 150 mL of methanol then stirred at 0° C. for 4 h. The precipitate was suction filtered (mother liquors are recycled to complete the transfer), washed with 100 mL of 0° C. methanol, washed with three times with 100 mL of $H_2O$, then air dried at 25° C. for 17 h to afford 76.90 g of colorless solid. The solid (72.09 g) was re-slurried in 700 mL of $H_2O$ at 25° C. After stirring for about 2 h, the solid was suction filtered, washed with 200 mL of $H_2O$, and air dried at 25° C. for 70 h to afford 41.30 g of colorless solid.

NMR analysis of another run indicated complete conversion in 5–6 h at 0° C.

Theoretical Yield=64.50 g based on (R)-3-hydroxytetradecanoic acid.

Example 7

This example illustrates a method for preparing trimethylsilyl (R)-3-(trimethylsiloxy)tetradecanoate using HMDS.

A 1000-mL, 3-necked flask was fitted with condenser/nitrogen adapter, paddle stirrer, and 250-mL pressure-equilibrating addition funnel/septum. The reactor was charged with 45.00 g (184.1 mmol) of (R)-3-hydroxytetradecanoic acid from Example 2. The flask was sealed, nitrogen was started, 290 mL of dry THF was added via cannula, and stirring (200 rpm) was started. The addition funnel was charged with 38.9 mL (29.72 g, 184.1 mmol) of hexamethyldisilazane (HMDS). The HMDS was then added dropwise at 20–25° C. over 15 min. The addition funnel was rinsed with 10 mL of dry THF after the HMDS addition was completed. The suspension was heated to reflux (oil bath at 75° C.) over 4 min then refluxed for 2 h. The suspension was cooled to 25° C. then filtered under dry nitrogen (Teflon™ cannula and 60-mL airlessware funnel with medium frit). The flask and trace solids were washed with 50 mL of dry THF. The combined mother liquors were concentrated by distillation at atmospheric pressure (oil bath at 85° C.) (about 200 mL of THF collected). The pot solution (188.1 g of clear pale green liquid) can be used directly in the next step.

Example 8

This example illustrates a method for preparing diethyl 2-hexylmalonate.

A 5-L, 3-necked Morton flask with 2-L paddle stirrer was charged with sodium ethoxide (21 wt % in EtOH, 1000 mL, 2.801 moles) and 500 mL of absolute ethanol. Diethyl malonate (425 mL, 2.80 mol) in 50 mL of ethanol was added dropwise via a 500-mL pressure-equalized dropping funnel over 45 min at room temperature with stirring (150 rpm). Additional ethanol (250 mL) was added during the addition to redissolve precipitated salts. The funnel was washed with 150 mL of ethanol. The reaction mixture was heated to reflux and 1-bromohexane (432 mL (3.08 mol, 1.1 equiv) was added dropwise over 40 min. The funnel was washed with 50 mL of ethanol (total additional ethanol added about 1 L), and the reaction held at reflux for 2 h, after which the reaction mixture was neutral to moist litmus. The heat was removed and the reaction allowed to slowly cool to room temperature overnight. The reaction was then reheated to reflux and 1200 mL of ethanol distilled from the reaction mixture. Water (1 L) and heptane (500 mL) were added, the mixture transferred to a 4-L separatory funnel, and the layers separated. The organic layer was washed with 500 mL of saturated brine, dried with $MgSO_4$, and the solvent removed under reduced pressure. Crude product analysis (GC): 1-bromohexane ($T_R$=3.4 min, 4.3%); diethyl malonate ($T_R$=4.7 min, 2.9%); diethyl 2-hexylmalonate ($T_R$=10.7 min, 83.1%); diethyl 2,2-dihexylmalonate ($T_R$=14.9 min, 9.2%).

The crude product was transferred to a 1-L round-bottomed flask and a short-path distillation head connected. The crude mixture was gradually heated under 0.7 to 1.0 mm Hg of pressure to first distill off a fraction containing mostly 1-bromohexane (38–50° C.) followed by a second fraction (101 g, bp =55–100° C. at 0.95 mm Hg) which contained approximately 2% 1-bromohexane, 10% diethyl malonate, 87% diethyl 2-hexylmalonate, and 0.8% diethyl 2,2-dihexylmalonate (determined by GC). The main cut (459 g, bp=102–106° C. at 0.95 torr) contained no 1-bromohexane, 0.4% diethyl malonate, 96.7% diethyl 2-hexylmalonate, and 2.7% diethyl 2,2-dihexylmalonate. The pot bottoms contained 52 g material, which contained 22% diethyl 2-hexylmalonate and 77% diethyl 2,2-dihexylmalonate (by GC). Yield of diethyl 2-hexylmalonate in main fraction: 443.6 g (1.816 mol, 65%).

Example 9

This example illustrates a method for preparing dimethyl 2-hexylmalonate.

A 2-L, 3-necked Morton flask with 1-L paddle stirrer was charged with sodium methoxide (25 wt % solution in methanol, 460 mL, 2.01 mol) and 400 mL of HPLC grade methanol. A solution of dimethyl malonate (216 mL, 250 g, 1.89 mol) in 90 mL of methanol was added dropwise via a 500-mL pressure-equalizing dropping funnel over 45 min with stirring (175 rpm). The reaction mixture became thick during addition due to precipitation; 110 mL of additional methanol was added to maintain efficient stirring (stirring rate increased to 350 rpm). The reaction mixture was then heated to reflux and 1-bromohexane (296 mL, 348 g, 2.11 mol) was added dropwise over 60 min. The funnel was washed with 50 mL of methanol, and the reaction mixture allowed to reflux overnight.

A short-path distillation head was attached, and 800 mL of methanol distilled from the reaction mixture. The reaction was then diluted with 300 mL of $H_2O$ and 700 mL of heptane, and stirred for 15 min. The mixture was transferred to a 4-L separatory funnel and the layers separated. The organic phase was washed with 300 mL of saturated brine, dried ($MgSO_4$), and concentrated under reduced pressure to give 399.5 g (98%) of crude product. Crude product analysis (GC): dimethyl malonate ($T_R$=4.5 min, 0.78%); 1-bromohexane ($T_R$=4.7 min, 1.0%); dimethyl 2-hexylmalonate ($T_R$=10.0 min, 84.5%); dimethyl 2,2-dihexylmalonate ($T_R$=13.2 min, 10.0%).

The crude product was transferred to a 1-L round bottomed flask connected to an 8" fractionating column and short-path distillation head. The crude mixture was slowly heated to 100° C. under 0.6 mm Hg of pressure to distill off a low-boiling forerun fraction containing solvent, 1-bromohexane, and dimethyl malonate. The bath was heated to 105° C. and an approximate 25 mL fraction was collected (b.p. 85–86° C., 0.62 mm Hg) followed by the main cut (b.p. 86–89° C., 0.66 mm Hg). The first fraction contained no 1-bromohexane or dimethyl malonate, 99.6% dimethyl 2-hexylmalonate, and 0.4% dimethyl 2,2-dihexylmalonate. The main cut (277.1 g) contained no 1-bromohexane or dimethyl malonate, 98.8% dimethyl 2-hexylmalonate, and 1.2% dimethyl 2,2-dihexylmalonate. The pot bottoms (59 g) contained 43% dimethyl 2-hexylmalonate and 56% dimethyl 2,2-dihexylmalonate (GC). Yield of dimethyl 2-hexylmalonate in first two fractions: 295.1 g (1.365 mol, 72%).

Example 10

This example illustrates a method for preparing 2-(ethoxycarbonyl)octanoic acid, i.e., ethyl hexylmalonate half-acid.

To a solution of diethyl 2-hexylmalonate of Example 8 (244.36 g, 1.000 mol) in 25 mL of absolute ethanol in a 2-L, 3-necked Morton flask was added a solution of potassium hydroxide (59.9 g, 0.907 mol)(weight adjusted for 85% assay of commercial potassium hydroxide) in 450 mL of absolute ethanol dropwise via a 500-mL pressure-equalizing dropping funnel over 75 min. The funnel was washed with 25 mL of absolute ethanol. The reaction mixture was stirred for 2 h, and 300 mL of ethanol was then removed under reduced pressure. Water (500 mL) was added, and the mixture extracted with 500 mL of heptane to remove unreacted diethyl 2-hexylmalonate. The aqueous solution was acidified with 12 M HCl to pH 2 then extracted with 500 mL of heptane. The heptane solution was dried (MgSO$_4$) and the solvent removed under reduced pressure to give 2-(ethoxycarbonyl)octanoic acid as a colorless oil. Traces of ethanol were removed by adding 20 mL of toluene to the crude product, followed by stripping of the solvent at 1 mm Hg of pressure with stirring. The yield was 190.9 g (0.8827 mol, 88.3% based on diethyl 2-hexylmalonate, 97% based on potassium hydroxide).

Example 11

This example illustrates a method for preparing 2-(methoxycarbonyl)octanoic acid, i.e., methyl hexylmalonate half-acid.

A solution of dimethyl 2-hexylmalonate of Example 9 (220.35 g, 1.019 mol) in 500 mL of methanol was prepared in a 2-L round-bottomed flask with magnetic stirring. A solution of potassium hydroxide (60.8 g, 0.921 mol) in 500 mL of methanol was added dropwise at 20–25° C. (H$_2$O bath) over 60 min with stirring. The reaction was stirred for 2 h then 950 mL of methanol was removed under reduced pressure on a rotary evaporator. A 1 L mixture of 1:1 H$_2$O and heptane was added, and the layers separated in a 2-L separatory funnel. The aqueous layer was acidified with 12 M HCl to pH 1. The suspension was then extracted with 500 mL of heptane and the heptane solution dried (MgSO$_4$) and concentrated to give a cloudy oil (suspended salts). Toluene (200 mL) was added, and the mixture was allowed to stand for 21 h. The suspension was filtered and the solvent evaporated under reduced pressure to give 182.53 g of 2-(methoxycarbonyl)octanoic acid as a clear oil (0.902 mol, 88.5% based on dimethyl 2-hexylmalonate, 98% based on potassium hydroxide).

Example 12

This example illustrates a method for preparing 3-(trimethylsiloxy)tetradecanoyl chloride.

A 500-mL, 3-necked Morton flask was charged with (R)-3-hydroxytetradecanoic acid of Example 2 (20.06 g, 82.09 mmol) and 90 mL of dry THF under N$_2$ with magnetic stirring. Hexamethyl-disilazane (HMDS, 17.3 mL, 82.0 mmol, 1.00 equiv) was added via syringe, and the reaction mixture heated to reflux for 2 h then allowed to cool to 20–25° C. The reaction was checked by $^1$H NMR, which showed clean conversion to trimethylsilyl (R)-3-(trimethylsiloxy)tetradecanoate. The reaction was cooled to 0° C. while monitoring the internal temperature then pyridine (0.34 mL, 4.2 mmol, 5 mol %) was added via syringe followed by thionyl chloride (6.6 mL, 90.5 mmol, 1.1 equiv), which was added over 6 min. The reaction was stirred at 0° C. for 140 min, and checked by $^1$H NMR, which showed about 3% trimethylsilyl (R)-3-(trimethylsiloxy) tetradecanoate and a small amount of a degradation product.

Dry heptane (90 mL) was added, and the reaction stirred for 30 min and filtered under dry nitrogen (Teflon™ cannula and 200-mL coarse-fritted airlessware funnel) into a dry 1-L, 3-necked, round-bottomed flask. The flask and funnel were washed with 50 mL of heptane. The solvent was evaporated under gradually increasing vacuum (50 to 8 mm Hg using a Vacuubrand™ vacuum pump) at 0° C. over 2 h to give 3-(trimethylsiloxy)-tetradecanoyl chloride as a yellow oil, which was used directly in the next step.

Example 13

This example illustrates a method for preparing ethyl 5-hydroxy-2-hexyl-3-oxohexadecanoate.

A 1-L, 3-necked Morton flask fitted with a mechanical stirrer (500 mL-paddle) was charged with 2-(ethoxycarbonyl)-octanoic acid from Example 10 (21.34 g, 98.67 mmol) and 150 mL of dry THF. Triethylamine (28.0 mL, 201 mmol, 2.04 equiv) was added followed by magnesium chloride (Aldrich; water content <1.5%; 9.67 g, 102 mmol, 1.03 equiv) at room temperature. The reaction was stirred for 105 min (150 rpm) at room temperature then cooled to 0° C. A racemic mixture of 3-(trimethylsiloxy)-tetradecanoyl chloride (82.1 mmol, 0.83 equiv) in about 30 mL of heptane was added dropwise over 15 min via a 50-mL pressure-equalizing addition funnel. The funnel was washed with 20 mL of THF (total THF=170 mL), and the reaction was stirred for 15 h (150 rpm) while warming to rt. The reaction was then cooled to 0° C., and 80 mL of 3 M HCl (3 equiv) was added dropwise over 9 min followed immediately by 150 mL of heptane. The mixture was stirred for 15 min, and the layers separated. The organic layer was washed once with 100 mL of water and twice with 50 mL of saturated NaHCO$_3$. The organic layer was dried (MgSO$_4$) and the solvent removed under reduced pressure to give 32.05 g of crude product.

$^1$H NMR analysis showed ethyl 5-hydroxy-2-hexyl-3-oxohexadecanoate as the major product.

300 MHz $^1$H NMR (CDCl$_3$) δ 0.88 (m, 6H), 1.26 (m, 29H), 1.43 (m, 2H), 1.84 (m, 2H), 2.57, 2.71 (m, 2H), 2.88 (m, 1H), 3.42 (m, 1H), 4.04 (m, 1H), 4.19 (q, 2H).

Example 14

This example illustrates the effect of reaction conditions on the yield of 3-4-hydroxy-6-undecyl-5,6-dihydropyran-2-one from ethyl (5R)-2-hexyl-5-hydroxy-3-adecanoate.

Ethyl (5R)-2-hexyl-5-hydroxy-3-oxohexadecanoate was subjected to a variety tion conditions to produce 3-hexyl-4-hydroxy-6-undecyl-5,6-dihydropyran-2-one. The are shown in Table 1.

TABLE 1

Cyclization of ethyl (5R)-2-hexyl-5-hydroxy-3-oxohexa-decanoate to 3-hexyl-4-hydroxy-6-undecyl-5,6-dihydropyran-2-one.

| Entry | Scale (g) | Acid/Base (equiv) | Solvent (mL) | Time (h) | Temp (° C.) | % yield |
|---|---|---|---|---|---|---|
| 1 | 1.26 | 12M HCl (0.08) | EtOAc (5) | 17 | 25 | 17 |
| 2 | 2.01 | 12M HCl (1.03) | EtOAc (8) | 22.5 | 25 | 34 |
| 3 | 2.00 | 0.5M HCl (1.0) | MTBE (15) | 22 | 25 | 0 |

TABLE 1-continued

Cyclization of ethyl (5R)-2-hexyl-5-hydroxy-3-oxohexa-decanoate to 3-hexyl-4-hydroxy-6-undecyl-5,6-dihydropyran-2-one.

| Entry | Scale (g) | Acid/Base (equiv) | Solvent (mL) | Time (h) | Temp (° C.) | % yield |
|---|---|---|---|---|---|---|
| 4 | 1.01 | None | 9:1 THF/H$_2$O (10 mL) | 20 | 60 | 0 |
| 5 | 2.06 | NaOMe (1.13) | MeOH (9) | 44 | 25 | 77 |
| 6 | 1.50 | H$_2$SO$_4$ (0.08) | MeOH (6) | 17 | 25 | 40 |
| 7 | 1.50 | 12M HCl (1.08) | MeOH (6) | 17 | 25 | 72 (63)[1] |
| 8 | 2.87 | 12M HCl (1.02) | MeOH (12) | 20 | 25 | 74 (65) |
| 9 | 2.00 | 12M HCl (1.04) | MeOH (8) | 20 | 25 | 59 |
| 10 | 2.00 | 12M HCl (1.04) | EtOH (8) | 20 | 25 | 38 |
| 11 | 3.87 | H$_2$SO$_4$ (1.02) | MeOH (16) | 22 | 25 | 64 |
| 12 | 31.35 | 12M HCl (1.03) | MeOH (125) | 27 | 25 | 63 (63) |
| 13 | 28.9 | 12M HCl (2.0) | MeOH (100) | 28 | 25 | 67 (61) |

( ) = yield from (R)-3-hydroxytetradecanoic acid using the malonate half-acid method.

Example 15

This example illustrates a method for preparing 3-hexyl-4-hydroxy-6-undecyl-5,6-dihydropyran-2-one.

A solution of crude racemic ethyl 5-hydroxy-2-hexyl-3-oxohexadecanoate of Example 13 (31.35 g, 78.64 mmol) was prepared in 125 mL methanol in a 1-L, 3-necked Morton flask with mechanical stirring. Hydrochloric acid (12 M, 6.6 mL, 81 mmol, 1.0 equiv) was added with stirring (150 rpm). After 1.5 h, 3-hexyl-4-hydroxy-6-undecyl-5,6-dihydropyran-2-one started to precipitate from the reaction mixture. After 26.5 h, the suspension was cooled to 0° C. and transferred to a 1 50-mL coarse-fritted funnel with 10 mL of cold methanol. The precipitate was filtered and washed twice with 15 mL of cold methanol to give 3-hexyl-4-hydroxy-6-undecyl-5,6-dihydropyran-2-one as a white crystalline solid (17.39 g, 49.3 mmol, 63% yield from 3-hydroxytetradecanoic acid).

Example 16

This example also illustrates the effect of different phosphine ligands on the ruthenium hydrogenation catalyst on the yield and %ee of asymmetric hydrogenation of β-ketoester.

The hydrogenation reaction of β-ketoester 1 of Example 17 was conducted using Ru(OAc)$_2$(diphosphine) with 20 equivalents of HCl at 60° C., under H$_2$ (70 bar) in methanol, with concentration of β-ketoester 1 at 30 % wt. The identity of diphosphine ligand, % isolated yield and (%ee) are shown below:

| Phosphine | Acronym | % yield[1] | % ee[2] |
|---|---|---|---|
| | BIPHEMP | 45 | 99 |
| | MeOBIPHEP | 28 | 99 |

-continued
| Phosphine | Acronym | % yield[1] | % ee[2] |
|---|---|---|---|
| 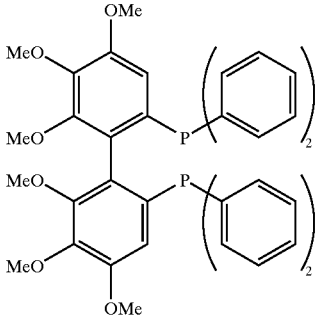 | TriMeOBIPHEP | 27 | 98 |
| 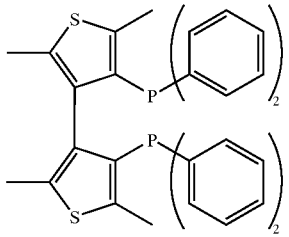 | TMBTP | 65 | 99 |
| 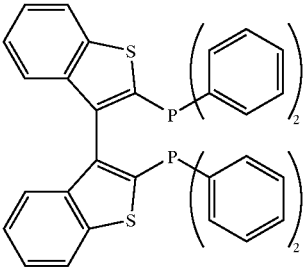 | BITIANP | nd | nd |
| 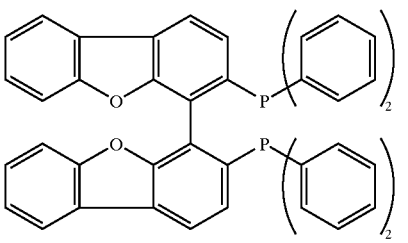 | BIBFUP | 17 | 97 |
| 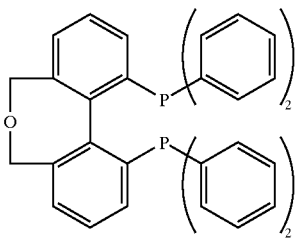 | BIPHOMP | nd | nd |

-continued

| Phosphine | Acronym | % yield[1] | % ee[2] |
|---|---|---|---|
| | mTol-BIPHEMP | 61 | 97 |
| | pTol-Me-OBIPHEP | 27 | 99 |
| | 3,5-tBu-MeOBIPHEP | 66 | 99 |
| | 3,5-tPe-MeOBIPHEP | 98 | 94 |

-continued
| Phosphine | Acronym | % yield[1] | % ee[2] |
|---|---|---|---|
| 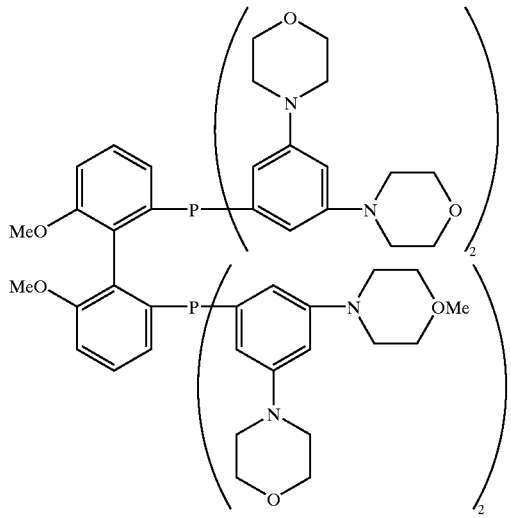 | 3,5-MOR-MeOBIPHEP | 13 | 75 |
| 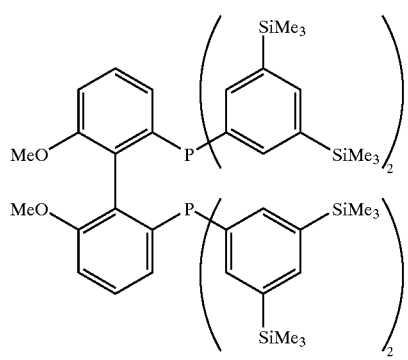 | 3,5-TMS-MeOBIPHEP | nd | nd |
| 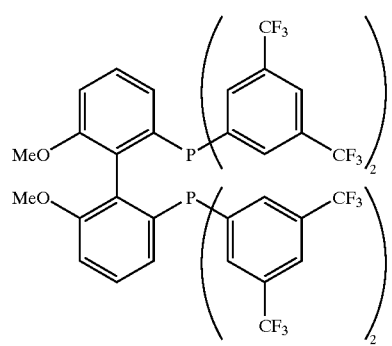 | 3,5-CF$_3$-MeOBIPHEP | nd | nd |

-continued

| Phosphine | Acronym | % yield[1] | % ee[2] |
|---|---|---|---|
| | 3,5-tBu-4-MeO-MeOBIPHEP | 50 | 96 |
| | 3,5-Xyl-4-MeO-MeOBIPHEP | 46 | 96 |
| | 3,5-iPr-4DMA-MeOBIPHEP | nd | nd |
| | 3,4,5-MeO-MeOBIPHEP | nd | nd |

-continued
| Phosphine | Acronym | % yield[1] | % ee[2] |
|---|---|---|---|
| 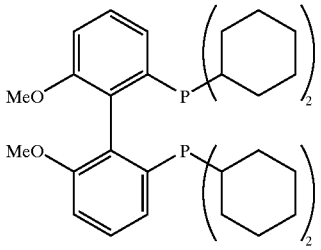 | Cy-MeOBIPHEP | 1 | nd |
| 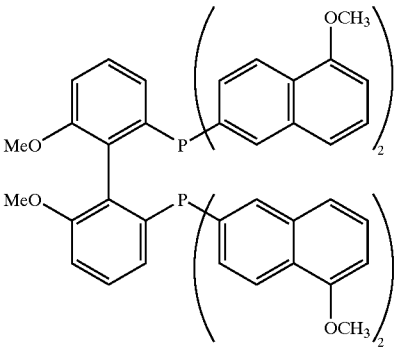 | 6-MeO-2-Naphthyl-MeOBIPHEP | 19 | 96 |
| 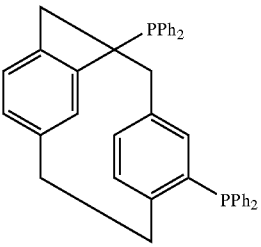 | PHANEPHOS | nd | nd |
| 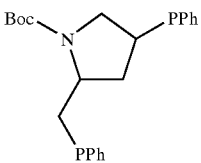 | BPPM | nd | nd |
| 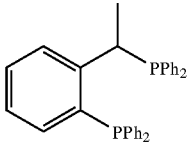 | MEBEP | 25 | 58 |
[1] % yield after 1 h
[2] % ee after 16 h
nd = not determined

Example 17

This example illustrates the effect of additives on the yield and %ee of asymmetric hydrogenation of β-ketoester.

TABLE 2

Asymmetric Hydrogenation: Influence of Additive*

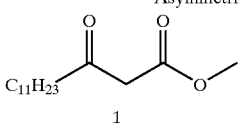

| | | conversion | | | | | 2 |
|---|---|---|---|---|---|---|---|
| entry[1] | Additive | 1h | 2h | 4h | 6h | 16h | % ee |
| 1 | 2 eq. HCl | 4 | 8 | 13 | 19 | 50 | 36(S) |
| 2 | 20 eq. HCl | 98 | >99.9 | | | | 99 |
| 3 | 20 eq. LiCl | 87 | 99.7 | 99.9 | >99.9 | | 97 |
| 4 | 20 eq. HBr | 31 | 59 | 78 | 82 | 91 | 46 |
| 5 | 20 eq. HBF$_4$ | 3 | 6 | 17 | 27 | 77 | 33(S) |
| 6 | 20 eq. p-TsOH | 50 | 79 | 96 | 98 | 99.8 | 62 |
| 7 | 2 eq. HCl + 4% wt.[2] CH$_2$Cl$_2$ | 32 | 66 | 90 | 97 | >99.9 | 71 |
| 8 | 2 eq. HCl + 18 eq. HBF$_4$ | 12 | 29 | 47 | 63 | 90 | 17(S) |
| 9 | 20 eq. Bu$_4$NI | <1 | <1 | <1 | <1 | <1 | — |

*Ratio of β-ketoester 1 to the catalyst = about 50,000:1.
[1]All gases >99.99990% purity.
[2]Relative to β-ketoester 1.

Example 18

This example illustrates the effect of different phosphine ligands on the ruthenium hydrogenation catalyst on the yield and %ee of asymmetric hydrogenation of β-ketoester.

TABLE 3

Asymmetric Hydrogenation: Influence of Phosphines*

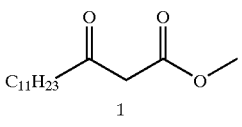

| | | conversion | | | | | 2 |
|---|---|---|---|---|---|---|---|
| entry[1] | Catalyst | 1h | 2h | 4h | 6h | 16h | % ee |
| 1* | [Ru(OAC)$_2$((R)-MeOBIPHEP)] | 26 | 48 | 94 | >99.9 | | 99 |
| 2* | [Ru(OAC)$_2$((R)-3,5-tBu-MeOBIPHEP)] | 66 | 99.5 | >99.9 | | | 99 |
| 3* | [Ru(OAc)$_2$((R)-BIPHEMP)] | 45 | 91 | >99.9 | | | 99 |
| 4* | [Ru(OAC)$_2$((S)-BINAP)] | 31 | 57 | 99.7 | >99.9 | | 96(S) |
| 5** | [Ru(OAC)$_2$((R,R)-NORPHOS)] | 7 | 14 | 27 | 39 | 90 | 64 |
| 6** | [Ru(OAC)$_2$((R,R)-CHIRAPHOS)$_2$] | <1 | <1 | <1 | <1 | 1 | — |

TABLE 3-continued

Asymmetric Hydrogenation: Influence of Phosphines[*]

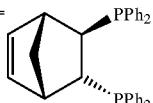

| entry[1] | Catalyst | 1h | 2h | 4h | 6h | 16h | % ee |
|---|---|---|---|---|---|---|---|
| 7[**] | [RuCl(p-cym)((R,R)-Me-DUPHOS)]Cl[2] | <1 | <1 | <1 | <1 | 1 | — |
| 8[**] | [RuCl(p-cym)((R)-MeOBIPHEP)]Cl[2] | 45 | 99 | >99.9 | | | 99 |

[*]Ratio of β-ketoester 1 to the catalyst = about 50,000:1
[**]Ratio of β-ketoester 1 to the catalyst = about 5,000:1
[1]All gases >99.99990% purity.
[2]No HCl used.

(R,R)-NORPHOS =

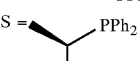

(R,R)-CHIRAPHOS =

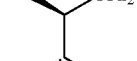

(R,R)-CHIRAPHOS =

, and p-cym = p-cymene.

Example 19

This example illustrates a method for producing (6R)-3-hexyl-5,6-dihydro-4-hydroxy-6-undecyl-pyran-2-one using tert-butylmagnesium chloride.

In a 500 mL 3-necked round bottom flask fitted with a Claisen head with $N_2$ inlet, a West condenser, a thermocouple-J-KEM controller and an addition funnel was added a solution of tert-butylmagnesium chloride (341 mL of a 1.0 M solution, 341 mmole, 3 equiv.) at about 60° C. Methyl-(R)-3-(2'-bromo-1'-oxooctyloxy)tetradecanoate (52.6.0 g, 113.5 mmole, 1 equiv.) and 25 mL of dry THF were added to an addition funnel. The starting bromodiester mixture was slowly added to the t-BuMgCl/THF mixture at reflux over about one hour. The reaction mixture was sampled at 1 and 2 hours at about 60° C. (resulting in 90 and 91% area normalized gas chromatography (AN GC) analysis, respectively). After 2 hours the resulting reaction mixture was cooled and concentrated on a roto-evaporator to about ⅓ to about ½ the original volume. The resulting syrupy mixture was taken up in about 250 mL of toluene and added to a mixture containing 250 mL of toluene, 75 mL of 10% HCl in a 1 L jacketed flask keeping the quenched solution below 30° C. The aqueous layer was removed. The organic layer washed one time with 50 mL of 1.0 N HCl solution. The aqueous layer was removed, the organic layer washed one time with 50 mL of water, dried over magnesium sulfate, filtered and concentrated. This resulted in a gel-like solid residue. The residue was dissolved in 250 mL of ethyl acetate at 40° C. The ethyl acetate was removed on the roto-evaporator. The resulting crude off-white solid (42.4 g) was slurried up in about 100 mL of hexane and cooled to 0° C., filtered and rinsed with 50 mL of cold hexane followed by another 25 mL of cold hexane. The isolated white solids were air dried under vacuum for about 1 to 2 hours resulting in 31.4 g of (6R)-3-hexyl-5,6-dihydro-4-hydroxy-6-undecyl-pyran-2-one (78.4% yield).

Example 20

This example illustrates a method for producing (6R)-3-hexyl-5,6-dihydro-4-hydroxy-6-undecyl-pyran-2-one using tert-amylmagnesium chloride.

In a 500 mL 3-necked round bottom flask fitted with a Claisen head with $N_2$ inlet, a West condenser, a thermocouple-J-KEM controller and an addition funnel, a solution of tert-amylmagnesium chloride (341 mL of a 1.0 M solution in $Et_2O$, 341 mmole, 3 equiv.) was added. The $Et_2O$ was replaced with THF and heated to about 60° C. Methyl-(R)-3-(2'-bromo-1'-oxooctyloxy)-tetradecanoate (52.6.0 g, 113.5 mmole, 1 equiv.) and 25 mL of dry THF was added to an addition funnel. The starting bromodiester mixture was slowly added to the t-amylMgCl/THF mixture at reflux over about one hour.

The reaction mixture was sampled at 1 and 2 hours at about 60° C. (resulting in 81 and 80% AN GC analysis, respectively). After about 2 hours the resulting reaction mixture was cooled and concentrated to about ⅓ to about ½ the original volume. The resulting syrupy mixture was diluted with about 250 mL of toluene and added to a stirred mixture containing about 250 mL of toluene and about 75 mL of 10% HCl in a 1 L jacketed flask while maintaining the quenched solution below about 30° C. The aqueous layer was removed. The organic layer was washed successively with about 50 mL of 1.0 N HCl solution and 50 mL of water, dried over magnesium sulfate, filtered and concentrated to yield a solid residue.

The residue was dissolved in about 400 mL of ethyl acetate at about 40° C. The ethyl acetate was removed on the roto-evaporator. The resulting crude off-white solid (42.3 g) was slurried up in about 100 mL of hexane and cooled to about 0° C., filtered and rinsed with about 50 mL of cold hexane followed by another about 35 mL of cold hexane. The isolated white solids were air dried under vacuum for about 1 to 2 hours resulting in 27.6 g of (6R)-3-hexyl-5,6-dihydro-4-hydroxy-6-undecyl-pyran-2-one (69.1 % yield).

Example 21

This example illustrates a process for producing β-ketoester 1 of Example 17.

Into a 250 mL three necked round bottomed flask equipped with a mechanical stirrer and reflux condenser under nitrogen was added 1.54 g of magnesium powder (99.5% pure, 50 mesh) and methanol (about 50 mL). The resulting mixture was heated to reflux overnight. The reflux condenser was replaced with a distillation head. Toluene (about 150 mL) was added and methanol was removed by azeotropic distillation until a head temperature of 104° C. was reached. Approximately 82 mL of distillate was collected.

To the resulting reaction mixture was added 29 g of methyl acetoacetate at 45° C. Methanol generated from the reaction was removed by distillation until a head temperature of about 104° C. was reached. Approximately 62 mL of distillate was collected. The reaction mixture was cooled to room temperature. The resulting mixture was then heated to about 60° C. and lauroyl chloride (20.71 g) in 20 mL of toluene was added over 2 hours, maintaining the reaction mixture at about 60° C. The resulting mixture was stirred for another 60 minutes. GC analysis showed that less than 1% lauroyl chloride remained.

Methanol (14.4 mL) was added and the resulting mixture was heated to about 70° C. and stirred for 4 hours. Another 9.0 mL of methanol was added and the resulting mixture was heated to 75° C. for an additional 20 hours. The resulting mixture was cooled to room temperature and the reaction was quenched by the addition of concentrated HCl (19.43 g) maintaining the temperature of the mixture below 35° C. The lower aqueous phase was separated, and the toluene phase was washed with water (2×45 mL), aqueous potassium bicarbonate (0.75 g in 36 mL of water), and then washed with water (36 mL). Toluene was removed under a rotoevaporator (75° C. at about 25–30 mmHg) to afford β-ketoester 1 of Example 17 in 86.6% yield (21.03 g, 92% A.N. by GC).

Example 22

This example illustrates a synthetic process for producing [Ru(OAc)$_2$((S)-BINAP)].

Under an argon atmosphere, a 25-mL 2-necked round-bottomed flask equipped with a reflux condenser was charged with (S)-BINAP (0.50 g. 0.80 mmol), 0.25 g (0.84 mmol) of [RuCl$_2$(COD)]$_n$, sodium acetate (0.33 g, 4.0 mmol) and toluene/acetic acid 1:1 (5 mL). The brown reaction mixture was stirred in an oil bath at 100° C. for 25 h. Thereafter, the volatiles were removed by rotatory evaporation, the residue was diluted with dichloromethane (5 mL) and the resulting yellow-brown suspension was filtered through celite. The filter cake was washed with dichloromethane (9 mL) in three portions, and the combined filtrates were concentrated and dried under high vacuum overnight at room temperature (r.t.). The brown oil was diluted in ether/hexane 1:1 (4 mL) and stirred for 30 min at r.t. to give a solid precipitate. The supernatant was removed by suction with a micro-filter candle and the residue was washed with hexane (5 nL) at r.t. and dried overnight. The crude product was diluted in methanol (5 mL) and stirred for 1 h at 50° C., 1 h at r.t. (formation of a precipitate), and finally 1 h at 0° C. The supernatant was removed as above, the residue was washed with methanol (2 mL) at 0° C. and dried overnight under high vacuum at r.t. to give [Ru(OAc)$_2$((S)-BINAP)] (0.48 g, 72% relative to S-BINAP) as a brown crystalline powder.

Example 23

This example illustrates a synthetic process for producing [Ru(OAc)$_2$((R)-BIPHEMP)].

Under an argon atmosphere a 50-mL 2-necked round-bottomed flask equipped with a reflux condenser was charged with (R)-BIPHEMP (2.01 g, 3.65 mmol), [RuCl$_2$(COD)]$_n$ (1.13 g, 3.83 mmol), sodium acetate (1.5 g, 18.2 mmol) and toluene/acetic acid 1:1 (20 mL). The brown reaction mixture was stirred in an oil bath at 100° C. for 31 h. The volatiles were removed by rotatory evaporation, the residue was diluted with dichloromethane (20 mL) and the, resulting yellow-brown suspension was filtered through celite. The filter cake was washed with dichloromethane (12 mL) in three portions and the combined filtrates were concentrated, diluted with methanol (10 mL) and stirred for 1 h at 50° C., 1 h at r.t. (formation of a precipitate), and finally 1 h at 0° C. The supernatant was removed by suction with a micro-filter candle, the residue was washed with methanol (6 mL) at 0° C. and dried overnight under high vacuum at r.t. to give [Ru(OAc)$_2$((R)-BIPHEMP)] (2.48 g, 88% relative to (R)-BIPHEMP) as a brown crystalline powder.

Example 24

This example illustrates a synthetic process for producing [Ru(OAc)$_2$((R)-3,5-t-Bu-MeOBIPHEP)].

Under an argon atmosphere a 25-mL 2-necked round-bottomed flask equipped with a reflux condenser was charged with (R)-3,5-tBu-MeOBIPHEP (0.50 g, 0.49 mmol), [RuCl$_2$(COD)]$_n$ (0.14 g, 0.51 mmol), sodium acetate (0.20 g, 2.44 mmol) and toluene/acetic acid 1:1 (5 mL). The brown reaction mixture was stirred in an oil bath at 100° C. for 26 h, and the volatiles were removed under high vacuum. The resulting residue was diluted with hexane (10 mL) and the resulting yellow-brown suspension was filtered through celite. The filter cake was washed with hexane (9 mL) in three portions and the combined filtrates were concentrated and dried overnight under high vacuum at r.t. yielding [Ru(OAc)$_2$((R)-3,5-t-Bu-MeOBIPHEP)] (0.62 g, 99% relative to (R)-3,5-t-Bu-MeOBIPHEP) as a brown crystalline powder.

Example 25

This example illustrates a synthetic process for producing [Ru((CH$_3$)$_3$CCO$_2$)$_2$((R)-MeOBIPHEP)].

Under an argon atmosphere a 25-mL 2-necked round-bottomed flask equipped with a reflux condenser was charged with (R)-MeOBIPHEP (1.06 g, 1.82 mmol), [RuCl$_2$(COD)]$_n$ (0.56 g. 2.00 mmol) and toluene (2 mL). To this mixture a solution obtained by dissolving sodium hydride (0.22 g, 9.1 mmol) in a mixture of toluene (3 mL) and pivalic acid (6.0 g, 59 mmol) was added and the resulting brown reaction mixture was stirred in an oil bath at 100° C. for 72 h, cooled, diluted with pentane (15 mL), and filtered through celite. The filter cake was washed successively with pentane (15 mL) in three portions and dichloromethane (25 ml) in four portions, the combined CH$_2$Cl$_2$ filtrates were concentrated and the resulting residue was dried overnight under high vacuum at r.t. The crude product was treated with methanol (10 mL) under stirring for 1 h at 50° C., 1 h at r.t., and finally 30 min at 0° C. The supernatant was removed by suction with a micro-filter candle, the residue was washed with methanol (5 mL) at 0° C. and dried overnight under high vacuum at r.t. to give [Ru((CH$_3$)$_3$CCO$_2$)$_2$((R)-MeOBIPHEP)] (0.66 g, 41% relative to (R)-MeOBIPHEP) as a brown crystalline give powder.

Example 26

This example illustrates a synthetic process for producing [Ru(OAc)$_2$(COD)].

Under an argon atmosphere a 50-mL 2-necked round-bottomed flask equipped with a reflux condenser was charged with [RuCl$_2$(COD)]$_n$ (1.01 g, 3.59 mmol), sodium acetate (1.47 g, 18.0 mmol and toluene/acetic acid 1:1 (20 ml). The brown reaction mixture was stirred in an oil bath at 100° C. for 4 h, the volatiles were removed by rotatory evaporation, and the residue was dried overnight under high vacuum at r.t. The resulting dark brown residue was diluted with toluene (10 mL) and filtered through celite. The filter cake was washed with toluene (15 mL) in three portions and the combined filtrates were concentrated. The resulting residue was diluted with dichloromethane (20 mL) and washed with water (8 mL) in two portions. The combined organic layers were dried over magnesium sulfate, filtered and the filter cake was washed with dichloromethane (15 mL) in three portions. The combined, yellow-brown filtrates were concentrated, and the resulting residue was diluted with pentane (5 mL), stirred for 30 min at 0° C., and the supernatant was removed by suction with a micro-filter candle. This process repeated and the resulting residue was dried overnight at r.t. to yield [Ru(OAc)$_2$(COD)] (0.57 g, 49%) as a light brown crystalline powder.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent compounds, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A process for producing a δ-lactone of the formula:

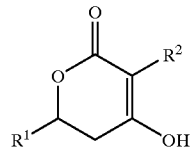

said process comprising the steps of:
(i)
 (a) treating an acyl halide of the formula:

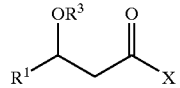

with a ketene acetal of the formula:

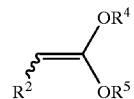

under conditions sufficient to produce a coupled intermediate; and
 (b) providing conditions sufficient to produce said δ-lactone I from said coupled intermediate, or
(ii)
 (a) treating an acyl halide of the formula:

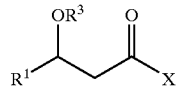

with a malonate half acid of the formula:

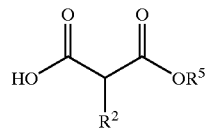

under conditions sufficient to produce a δ-hydroxy-β-ketoester of the formula:

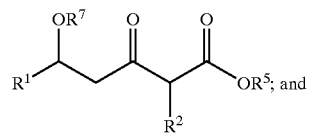

(b) treating said δ-hydroxy-β-ketoester with an acid under conditions sufficient to produce said δ-lactone, wherein
 $R^1$ is $C_1$–$C_{20}$ alkyl;
 $R^2$ is H or $C_1$–$C_{10}$ alkyl;
 $R^3$ is a hydroxy protecting group;
 each of $R^4$ and $R^5$ is independently $C_1$–$C_6$ alkyl, $C_5$–$C_{20}$ aryl, $C_6$–$C_{20}$ arylalkyl or —SiR$^8$R$^9$R$^{10}$;
 $R^7$ is H or $R^3$
 each of $R^8$, $R^9$, $R^{10}$ is independently $C_1$–$C_6$ alkyl or phenyl; and
 X is a halide.

2. The process of claim 1, wherein said coupled intermediate is a compound of the formula:

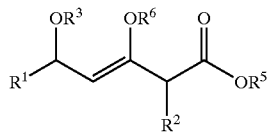

wherein $R^6$ is H or $R^4$; and $R^1$, $R^2$, $R^3$, $R^4$, and $R^5$ are those defined in claim 1.

3. The process of claim 2, wherein $R^6$ is $R^4$, and said step (b) comprises:

(i) removing $R^6$ or $R^3$ and $R^6$ to produce a deprotected intermediate; and (ii) contacting said deprotected intermediate with an acid under conditions sufficient to produce said δ-lactone.

4. The process of claim 3, wherein said deprotected intermediate is a δ-hydroxy-protected-β-ketoester of the formula:

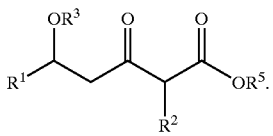

5. The process of claim 1, wherein $R^1$ is undecyl and $R^2$ is hexyl.

6. The process of claim 5, wherein X is chloride.

7. The process of claim 6, wherein $R^5$ is $C_1$–$C_6$ alkyl.

8. The process of claim 7, wherein each of $R^4$ and $R^6$ is a moiety of the formula —$SiR^8R^9R^{10}$.

9. The process of claim 8, wherein $R^7$ is H.

10. The process of claim 1 further comprising the step of producing said acyl halide, wherein said acyl halide producing step comprises:

(i) protecting a β-hydroxy acid of the formula:

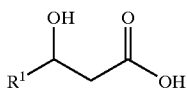

with a hydroxy protecting group to produce a β-hydroxy-protected ester of the formula:

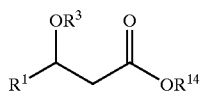

and (ii) contacting said β-hydroxy-protected ester with an acyl halogenating agent to produce said acyl halide, wherein $R^{14}$ is H, $R^3$ or a carboxylate counter cation.

11. The process of claim 10, wherein each of $R^3$ and $R^{14}$ is a moiety of the formula —$SiR^{15}R^{16}R^{17}$, wherein each of $R^{15}$, $R^{16}$ and $R^{17}$ is independently $C_1$–$C_6$ alkyl or phenyl.

12. The process of claim 10 further comprising the step of enantioselectively producing said β-hydroxy acid, wherein said β-hydroxy acid producing step comprises:

(A) enantioselectively reducing a β-ketoester of the formula:

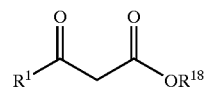

to enantioselectively produce a β-hydroxy ester of the formula:

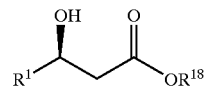

wherein $R^{18}$ is $C_1$–$C_6$ alkyl, $C_5$–$C_{20}$ aryl or $C_6$–$C_{20}$ arylatkyl; and (B) saponifying said β-hydroxy ester to produce said β-hydroxy acid.

13. The process of claim 12, wherein said process produces said δ-lactone having the following stereochemical configuration:

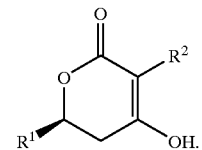

14. The process of claim 13, wherein said process produces said δ-lactone in an enantiomeric excess of at least about 90%.

15. The process of claim 12, wherein said step of enantioselective reduction of said β-ketoester comprises hydrogenation of said β-ketoester in the presence of a hydrogenation catalyst.

16. The process of claim 15, wherein said hydrogenation catalyst is a compound of the formula $RuCl_2((R)$-MeOBIPHEP).

17. The process of claim 15, wherein said hydrogenation catalyst is the product produced by contacting a ruthenium diacetate compound of the formula $Ru(OAc)_2((R)$-MeOBIPHEP) with a halide source.

18. The process of claim 17, wherein the molar ratio of between said halide source and said ruthenium diacetate is at least about 20:1.

19. A process for enantioselective preparation of a β-hydroxy ester of the formula:

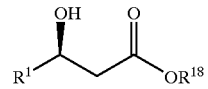

comprising hydrogenating a β-ketoester of the formula:

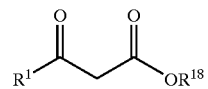

in the presence of about 40 bar of pressure or less of hydrogen gas and a ruthenium hydrogenation catalyst comprising a halide and a chiral substituted biphenyl phosphorous ligand, wherein $R^1$ is $C_{1-20}$ alkyl, and $R^{18}$ is H or $C_1$–$C_6$ alkyl, $C_5$–$C_{20}$ aryl or $C_6$–$C_{20}$ arylalkyl.

20. The process of claim 19, wherein said hydrogen gas is technical grade hydrogen gas.

21. The process of claim 19, wherein $R^1$ is undecyl.

22. The process of claim 21, wherein $R^{18}$ is $C_1$–$C_6$ alkyl.

23. The process of claim 19, wherein said hydrogenation catalyst is a compound of the formula $RuCl_2((R)\text{-MeOBIPHEP})$.

24. The process of claim 19, wherein said hydrogenation catalyst is the product produced by contacting a ruthenium diacetate compound of the formula $Ru(OAc)_2((R)\text{-MeOBIPHEP})$ with a halide source.

25. The process of claim 24, wherein the molar ratio of between said halide source and said ruthenium diacetate is at least about 20:1.

26. A process for enantioselectively producing a δ-lactone of the formula:

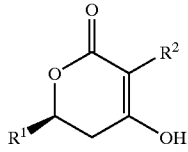

said process comprising the steps of:

(i)

(a) reacting an acyl halide of the formula:

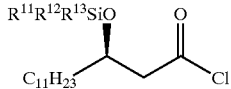

with a silyl ketene acetal of the formula:

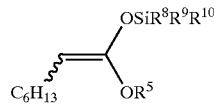

under conditions sufficient to produce a δ-siloxy-β-silyl enol ether ester of the formula:

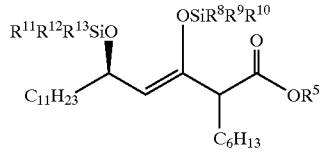

(b) contacting said δ-siloxy-β-silyl enol ether ester with a base under conditions sufficient to remove at least one silyl group; and (c) contacting the product of said step (b) with an acid under conditions sufficient to produce said δ-lactone, or (ii)

(a) reacting an acyl halide of the formula:

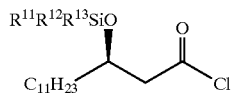

with a malonate half acid of the formula:

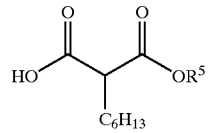

under conditions sufficient to produce a δ-hydroxy-β-ketoester of the formula:

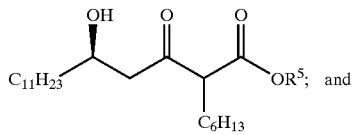

and (b) contacting said δ-hydroxy-β-ketoester with an acid under conditions sufficient to produce said δ-lactone, wherein $R^5$ is $C_1$–$C_6$ alkyl, $C_5$–$C_{20}$ aryl or $C_6$–$C_{20}$ arylalkyl; and each of $R^8$, $R^9$, $R^{10}$, $R^{11}$, $R^{12}$ and $R^{13}$ is independently $C_1$–$C_6$ alkyl or phenyl.

27. The process of claim 26, wherein said process produces said δ-lactone in an enantiomeric excess of at least about 90%.

28. The process of claim 26, wherein $R^5$ is $C_1$–$C_6$ alkyl.

29. The process of claim 26, wherein said acid is hydrochloric acid.

30. The process of claim 26, wherein said step (b) of option (i) comprises treating said δ-siloxy-β-silyl enol ether ester with a base selected from the group consisting of hydroxides and carbonates to remove both silyl groups.

31. The process of claim 26, wherein said step (b) of option (i) comprises treating said δ-siloxy-β-silyl enol ether ester with a bicarbonate to produce a δ-siloxy-β-ketoester of the formula:

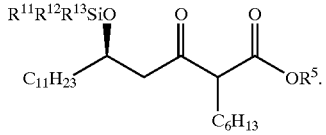

32. The process of claim 26 further comprising the step of producing said acyl halide, wherein said acyl halide producing step comprises:

(A) silylating (R)-3-hydroxy tetradecanoic acid with a silylating agent under conditions sufficient to produce a β-siloxy tetradecanoate silyl ester of the formula:

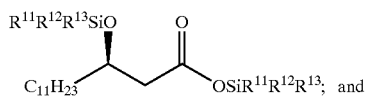

(B) contacting said β-siloxy tetradecanoate silyl ester with an acyl halogenating agent under conditions sufficient to produce said acyl halide.

33. The process of claim 32, wherein $R^{11}$, $R^{12}$ and $R^{13}$ are methyl.

34. The process of claim 33, wherein said silylating agent is selected from the group consisting of trimethylsilyl chloride and hexamethyldisilazane.

35. The process of claim 32, wherein said acyl halogenating agent is thionyl chloride.

36. The process of claim 32 further comprising the step of producing said (R)-3-hydroxy tetradecanoic acid, wherein said (R)-3-hydroxy tetradecanoic acid producing step comprises:

(a1) enantioselectively reducing a β-ketoester of the formula:

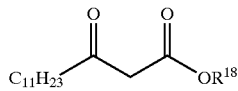

to produce a β-hydroxy ester of the formula:

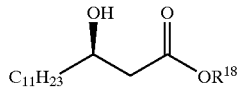

wherein
$R^{18}$ is $C_1$–$C_6$ alkyl, $C_5$–$C_{20}$ aryl or $C_6$–$C_{20}$ arylalkyl; and (a2) saponifying said β-hydroxy ester to produce said (R)-3-hydroxy tetradecanoic acid.

37. The process of claim 36, wherein said step of enantioselective reduction of said β-ketoester comprises hydrogenation of said β-ketoester in the presence of a hydrogenation catalyst.

38. The process of claim 37, wherein said hydrogenation catalyst is selected from the group consisting of a compound of the formula RuCl$_2$((R)-MeOBIPHEP) and a product produced by contacting a ruthenium diacetate compound of the formula Ru(OAc)$_2$((R)-MeOBIPHEP) with a halide source.

39. The process of claim 38, wherein said hydrogenation catalyst is the product produced by contacting a ruthenium diacetate of the formula Ru(OAc)$_2$((R)-MeOBIPHEP) with said halide source.

40. The process of claim 39, wherein the molar ratio of between said halide source and said ruthenium diacetate is at least about 20:1.

41. A compound selected from the group consisting of β-siloxy acyl halides of the formula:

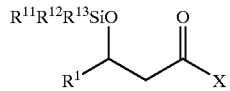

δ-siloxy-β-silyl enol ether esters of the formula:

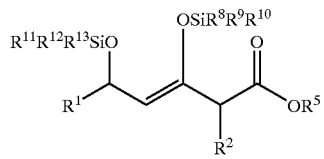

and δ-siloxy-β-ketoesters of the formula:

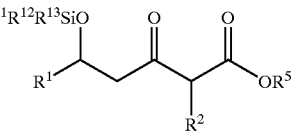

wherein
$R^1$ is $C_1$–$C_{20}$ alkyl;
$R^2$ is H or $C_1$–$C_{10}$ alkyl;
$R^5$ is $C_1$–$C_6$ alkyl, $C_5$–$C_{20}$ aryl or $C_6$–$C_{20}$ arylalkyl;
each of $R^8$, $R^9$, $R^{10}$, $R^{11}$, $R^{12}$ and $R^{13}$ is independently $C_1$–$C_6$ alkyl or phenyl; and
X is a halide.

42. The compound of claim 41, wherein said β-siloxy acyl halide is (R)-3-trimethylsiloxy tetradecanoyl chloride.

43. The compound of claim 41, wherein said δ-siloxy-β-silyl enol ether ester is selected from the group consisting of methyl (R)-3,5-bis-(trimethylsiloxy)-2-hexyl-3-hexadecenoate, and ethyl (R)-3,5-bis-(trimethylsiloxy)-2-hexyl-3-hexadecenoate.

44. The compound of claim 41, wherein said δ-siloxy-β-ketoester is selected from the group consisting of methyl (5R)-5-(trimethylsiloxy)-2-hexyl-3-oxo-hexadecanoate, and ethyl (5R)-5-(trimethylsiloxy)-2-hexyl-3-oxo-hexadecanoate.

* * * * *